(12) United States Patent
Yoshikawa et al.

(10) Patent No.: US 10,667,866 B2
(45) Date of Patent: Jun. 2, 2020

(54) TREATMENT SUPPORT APPARATUS AND TREATMENT SUPPORT METHOD

(71) Applicant: Hitachi, Ltd., Chiyoda-ku, Tokyo (JP)

(72) Inventors: Hideki Yoshikawa, Tokyo (JP); Shigeo Sumino, Tokyo (JP)

(73) Assignee: HITACHI, LTD., Tokyo (JP)

( * ) Notice: Subject to any disclaimer, the term of this patent is extended or adjusted under 35 U.S.C. 154(b) by 218 days.

(21) Appl. No.: 15/963,349

(22) Filed: Apr. 26, 2018

(65) Prior Publication Data
US 2018/0353242 A1 Dec. 13, 2018

(30) Foreign Application Priority Data
Jun. 12, 2017 (JP) ................................ 2017-114910

(51) Int. Cl.
| | |
|---|---|
| *G06T 7/00* | (2017.01) |
| *A61B 34/10* | (2016.01) |
| *A61B 5/01* | (2006.01) |
| *A61B 5/00* | (2006.01) |
| *A61B 5/02* | (2006.01) |

(52) U.S. Cl.
CPC .............. *A61B 34/10* (2016.02); *A61B 5/004* (2013.01); *A61B 5/015* (2013.01); *A61B 5/02007* (2013.01); *G06T 7/0012* (2013.01); *A61B 2034/104* (2016.02); *A61B 2034/105* (2016.02); *A61B 2576/02* (2013.01); *G06T 2207/10081* (2013.01); *G06T 2207/10088* (2013.01); *G06T 2207/30101* (2013.01)

(58) Field of Classification Search
CPC ........ A61B 2034/104; A61B 2034/105; A61B 2576/02; A61B 34/10; A61B 5/004; A61B 5/015; A61B 5/02007; G06T 2207/10081; G06T 2207/10088; G06T 2207/30101; G06T 7/0012
See application file for complete search history.

(56) References Cited

U.S. PATENT DOCUMENTS

2014/0296842 A1   10/2014   Mansi et al.

*Primary Examiner* — Nirav G Patel
(74) *Attorney, Agent, or Firm* — Procopio, Cory, Hargreaves & Savitch LLP

(57) ABSTRACT

Apparatus and methods are provided herein for providing treatment plan in which a position of a heat source and a treatment order are optimized.
An example treatment support apparatus includes a processor and a storage device connected to the processor. The storage device hold image information of tissue in a living body of a treatment target. The processor may extract a blood vessel structure of the inside of the living body from the image information, calculate positions of one or more heat sources for thermal treatment on a treatment scheduled region including at least a part of the extracted blood vessel structure on the basis of the extracted blood vessel structure, and output data for displaying an image including the calculated positions of the one or more heat sources.

14 Claims, 15 Drawing Sheets

[Fig. 1]
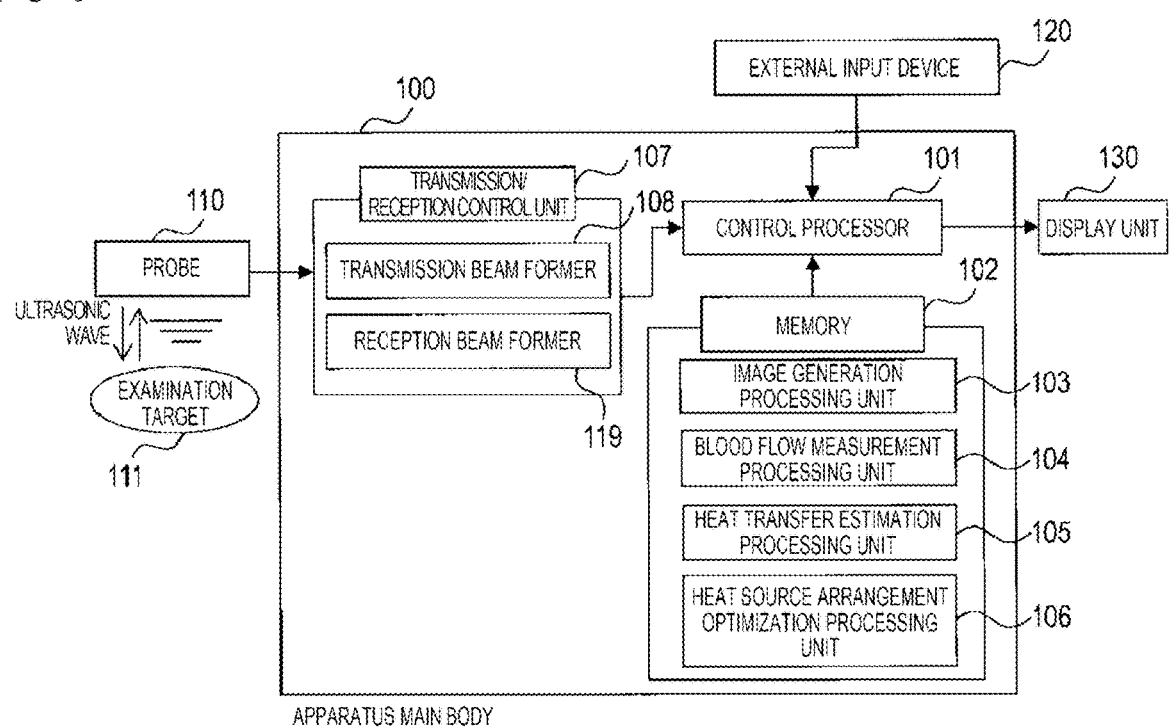

[Fig. 2]
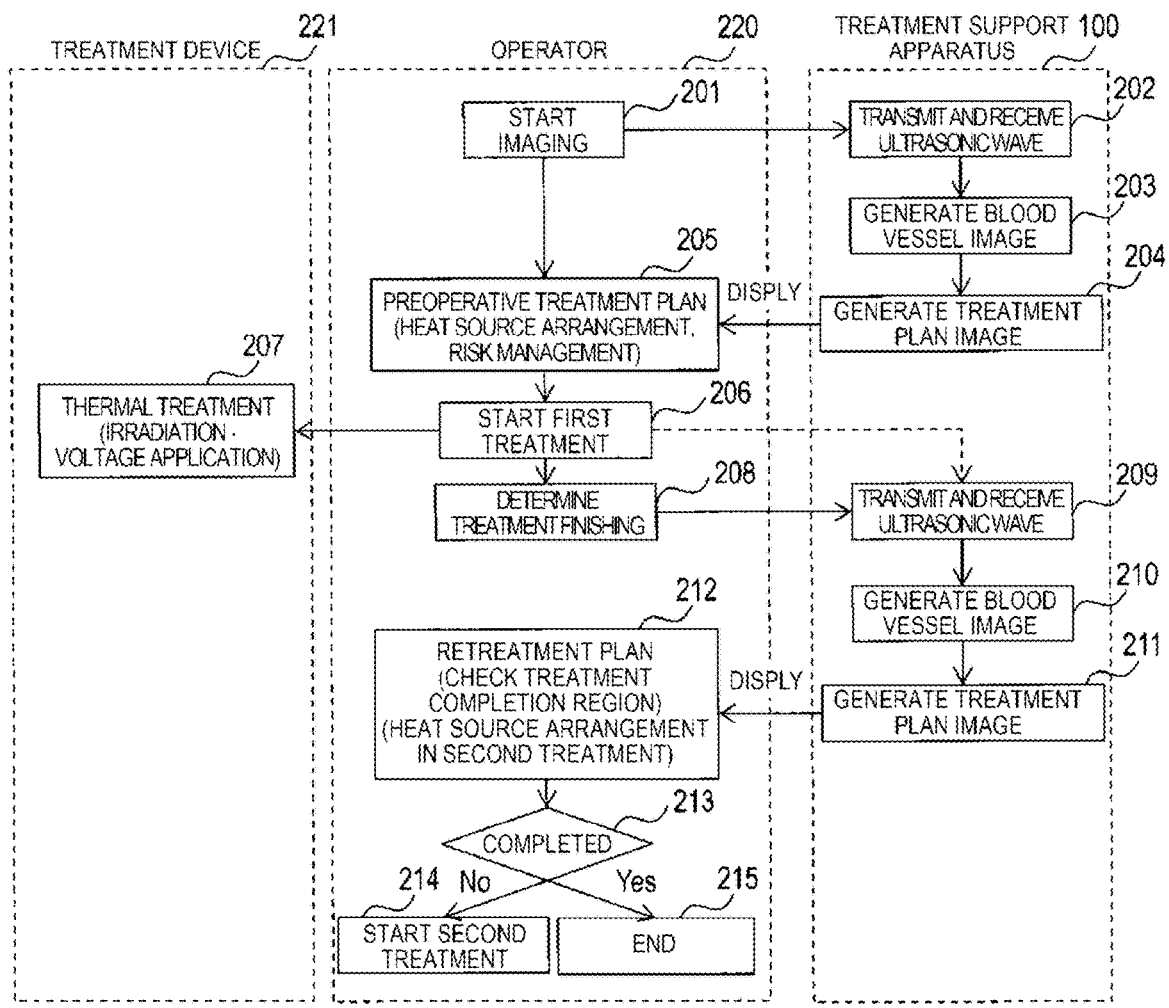

[Fig. 3]
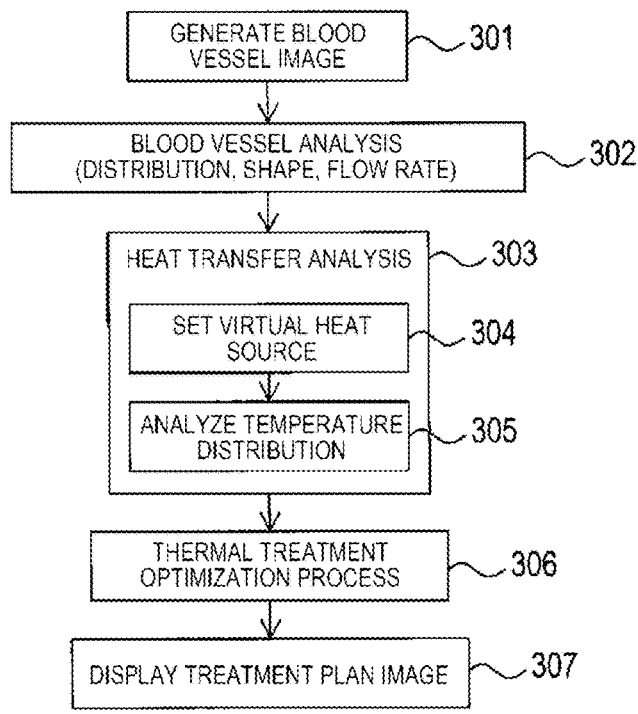
[Fig. 4]
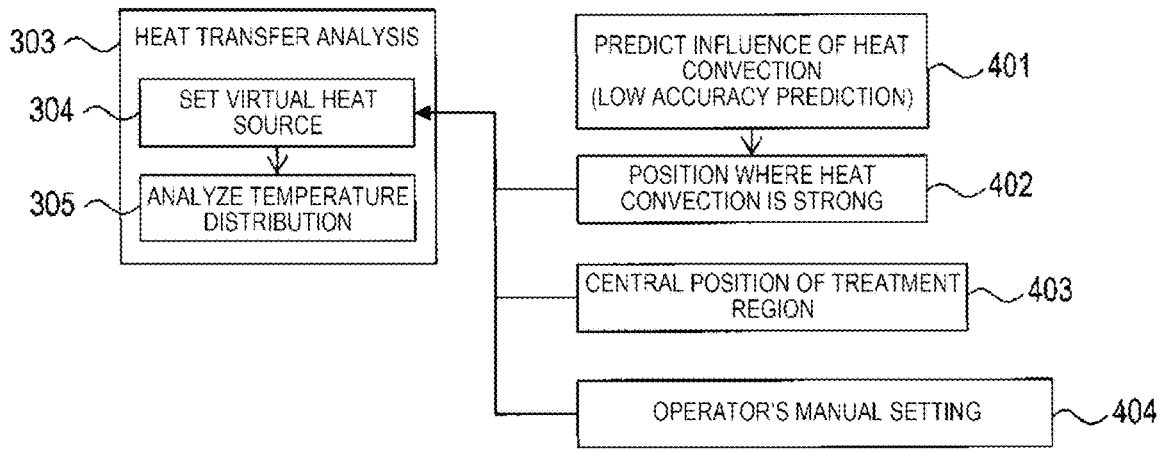

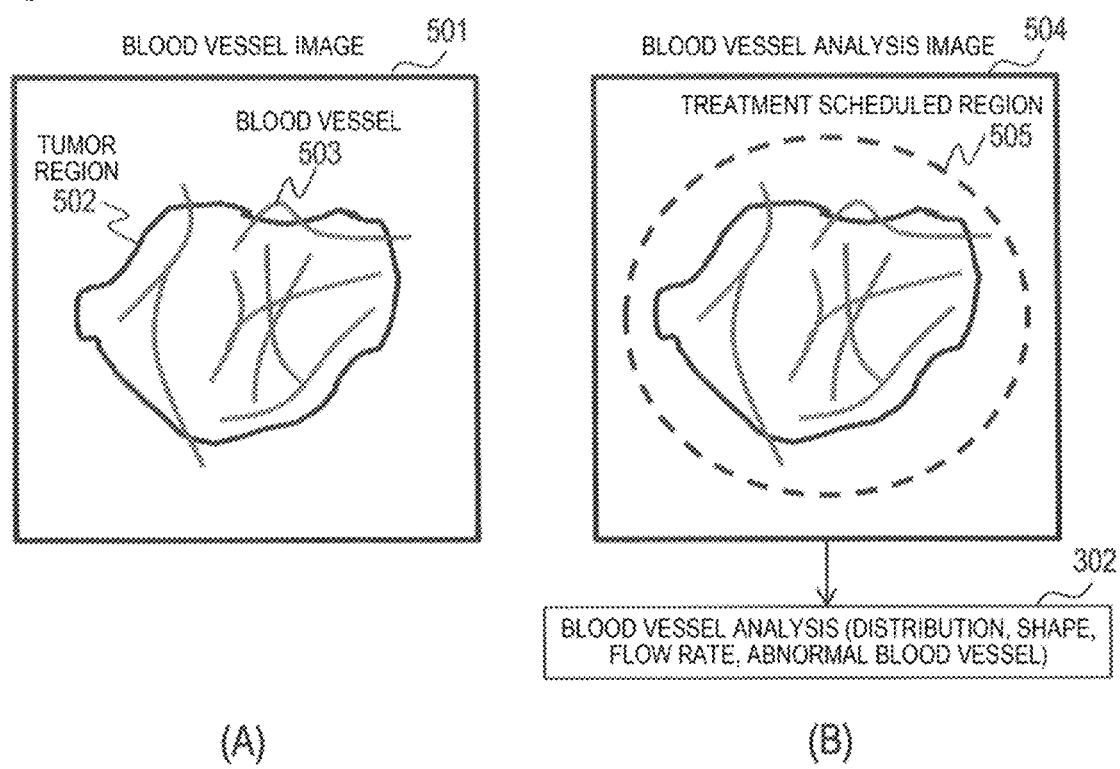

[Fig. 6]
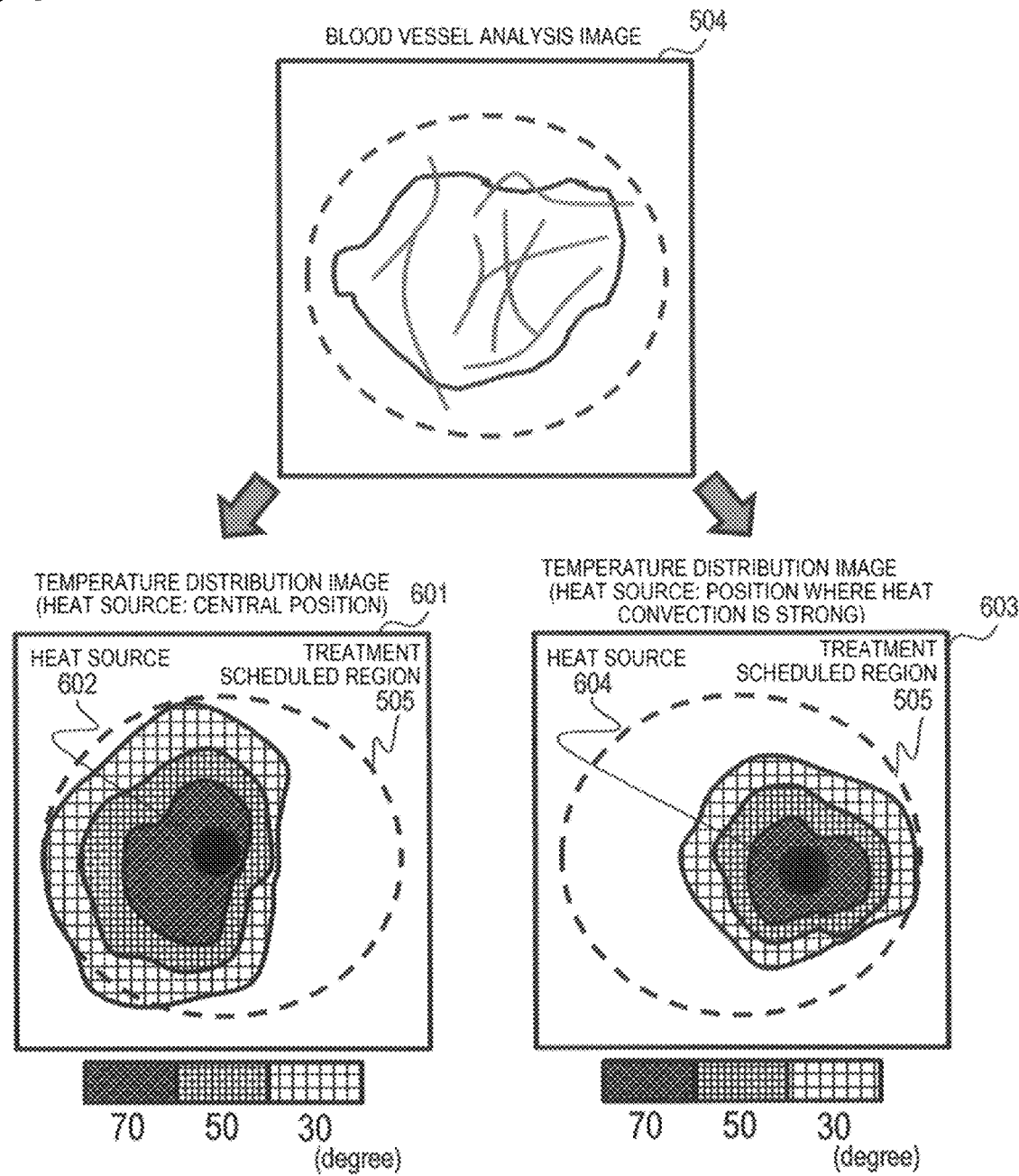

[Fig. 7]
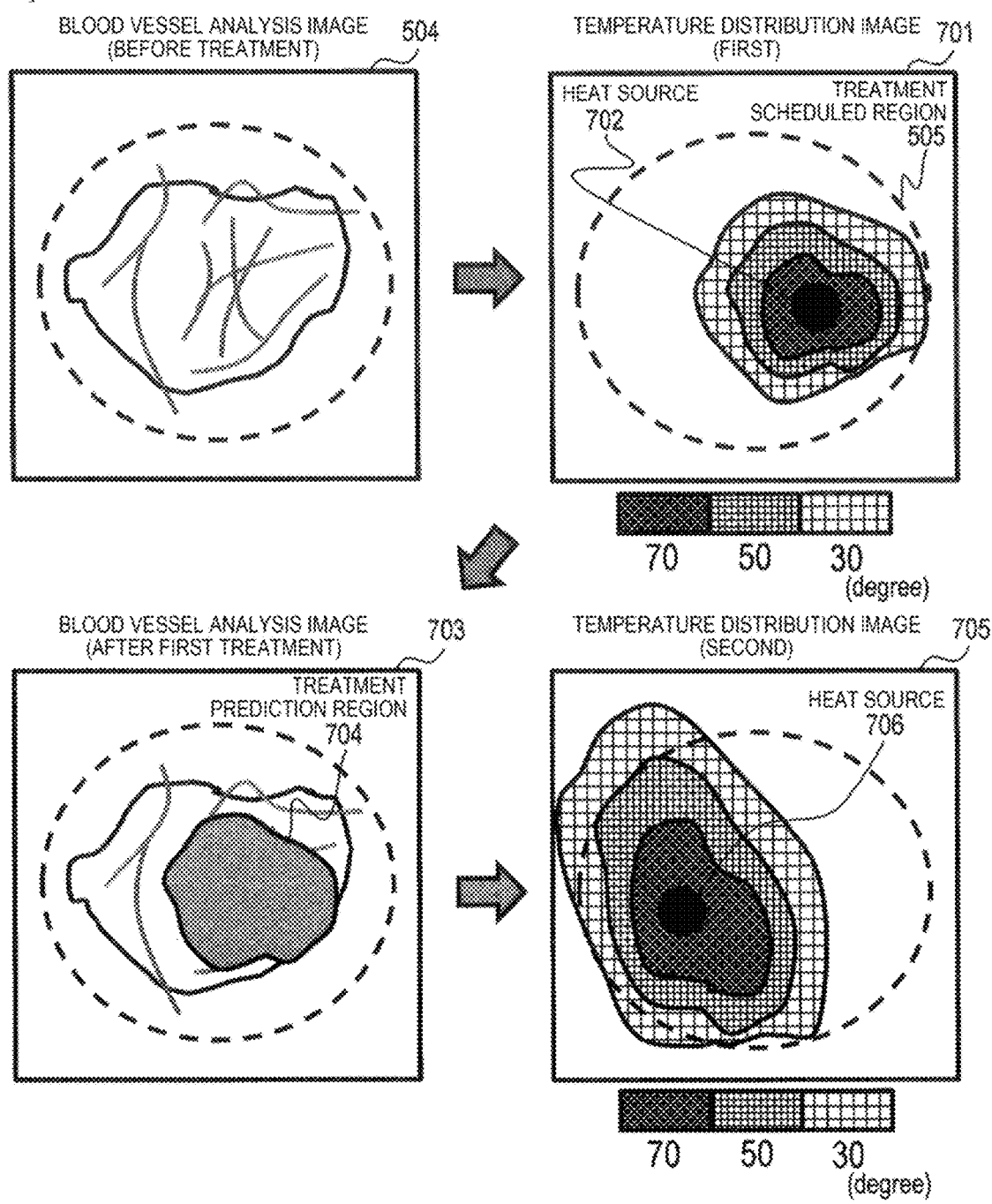

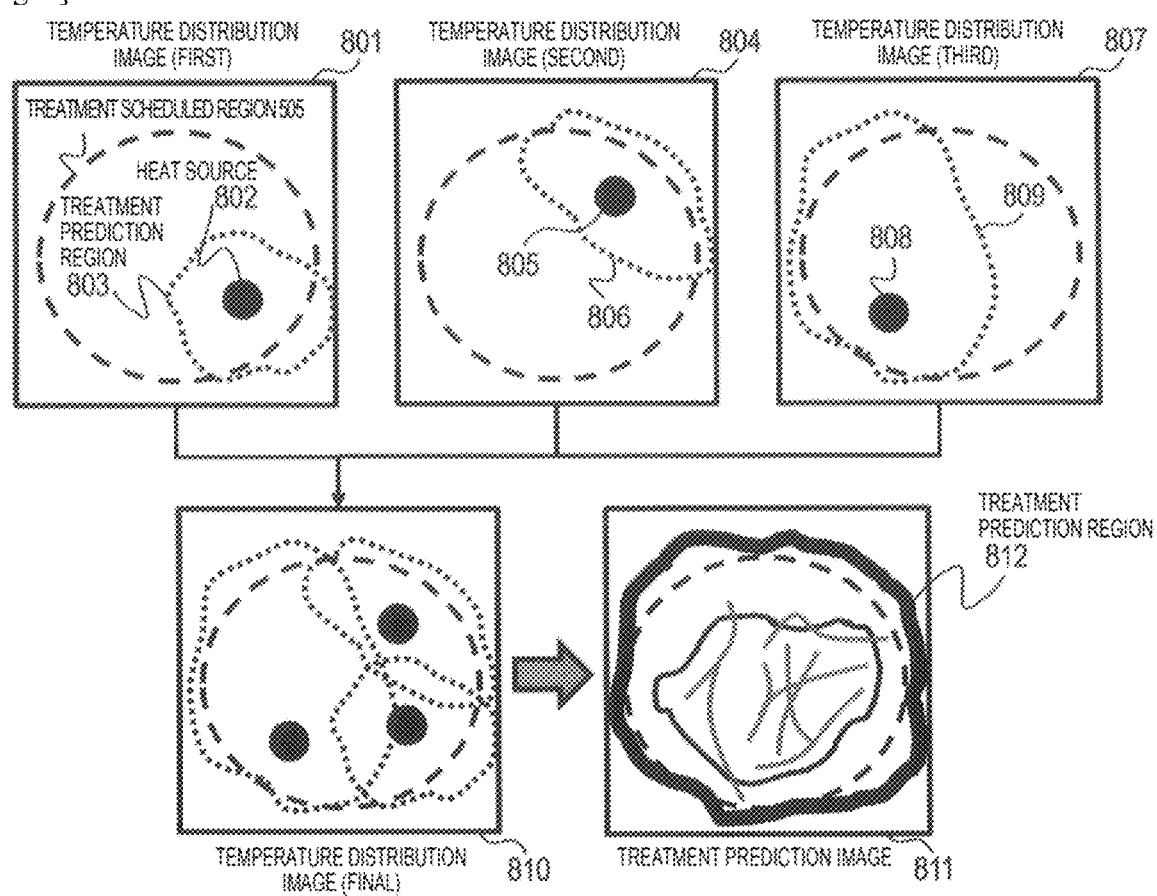
[Fig. 8]

[Fig. 9]
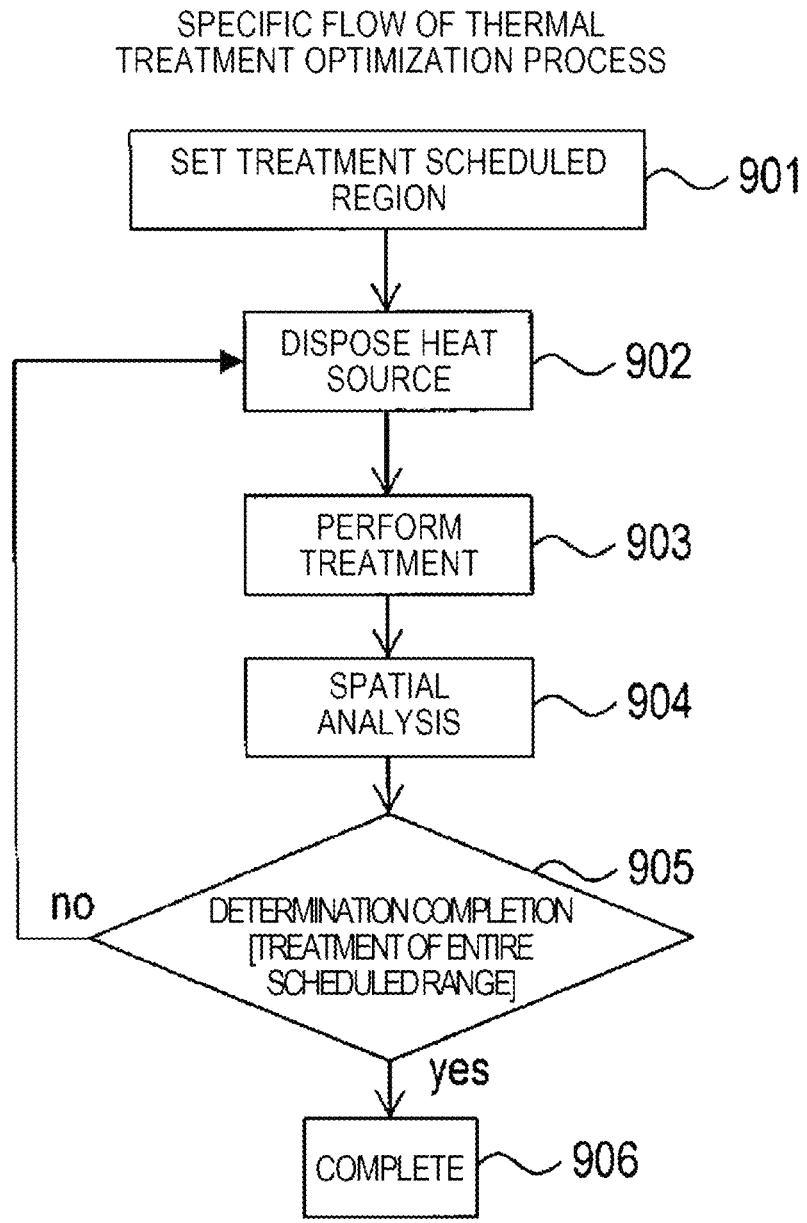

[Fig. 10]
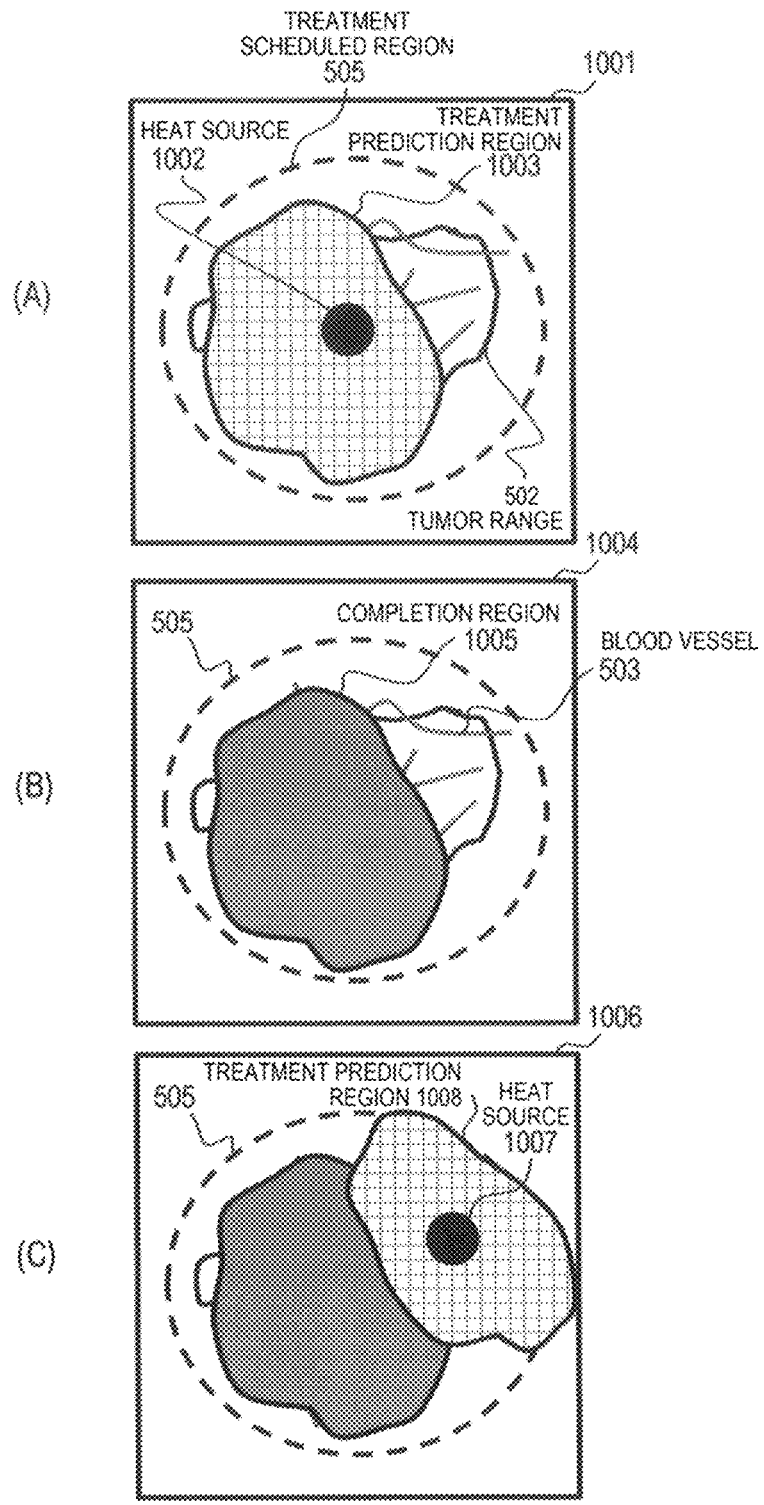

[Fig. 11]
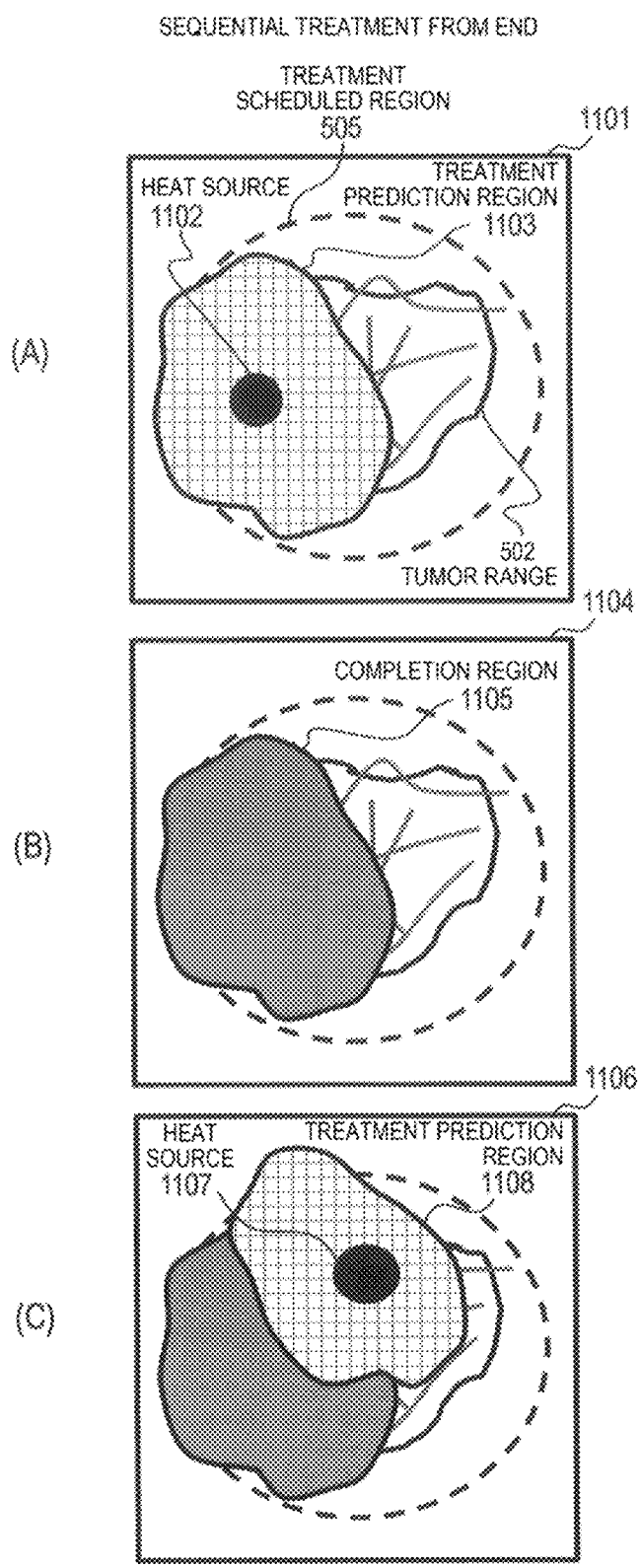

[Fig. 12]
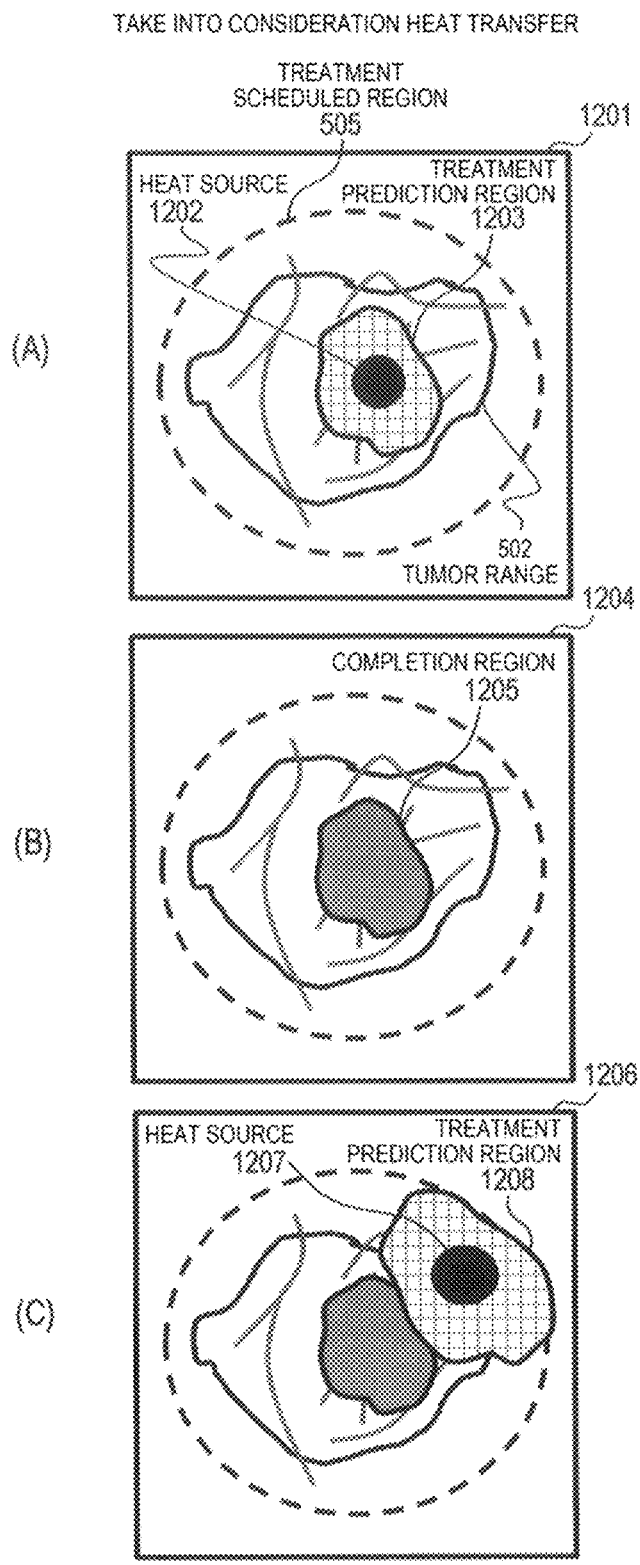

[Fig. 13]
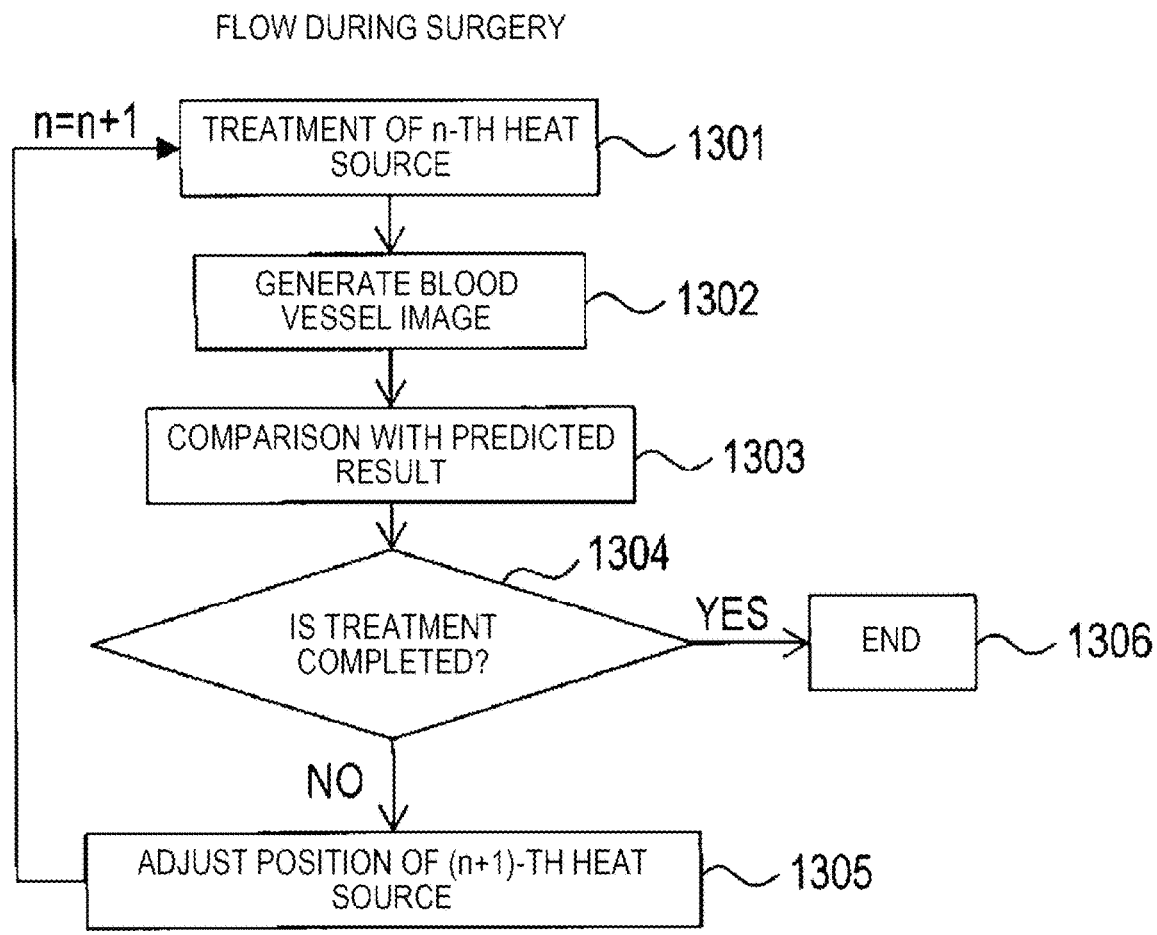

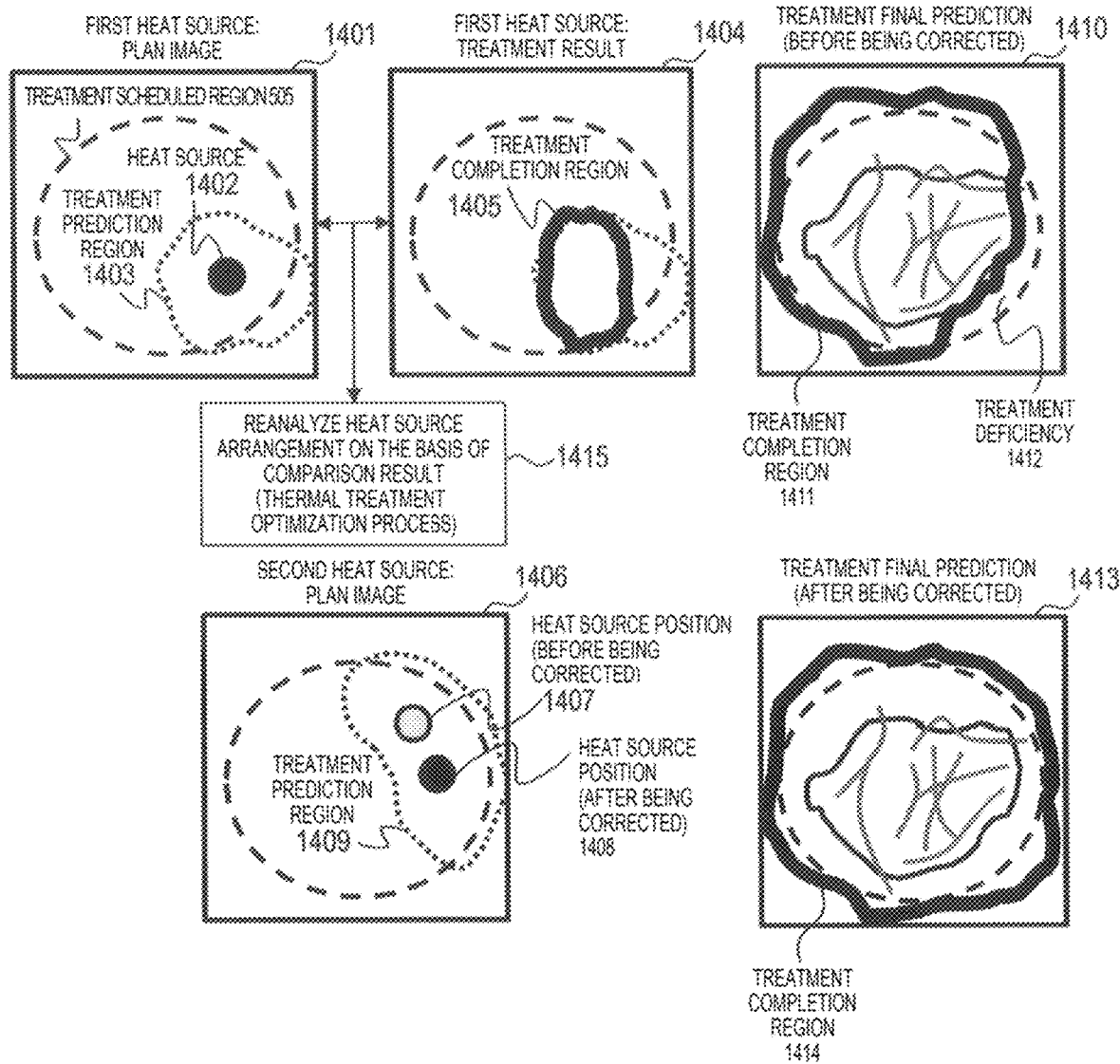
[Fig. 14]

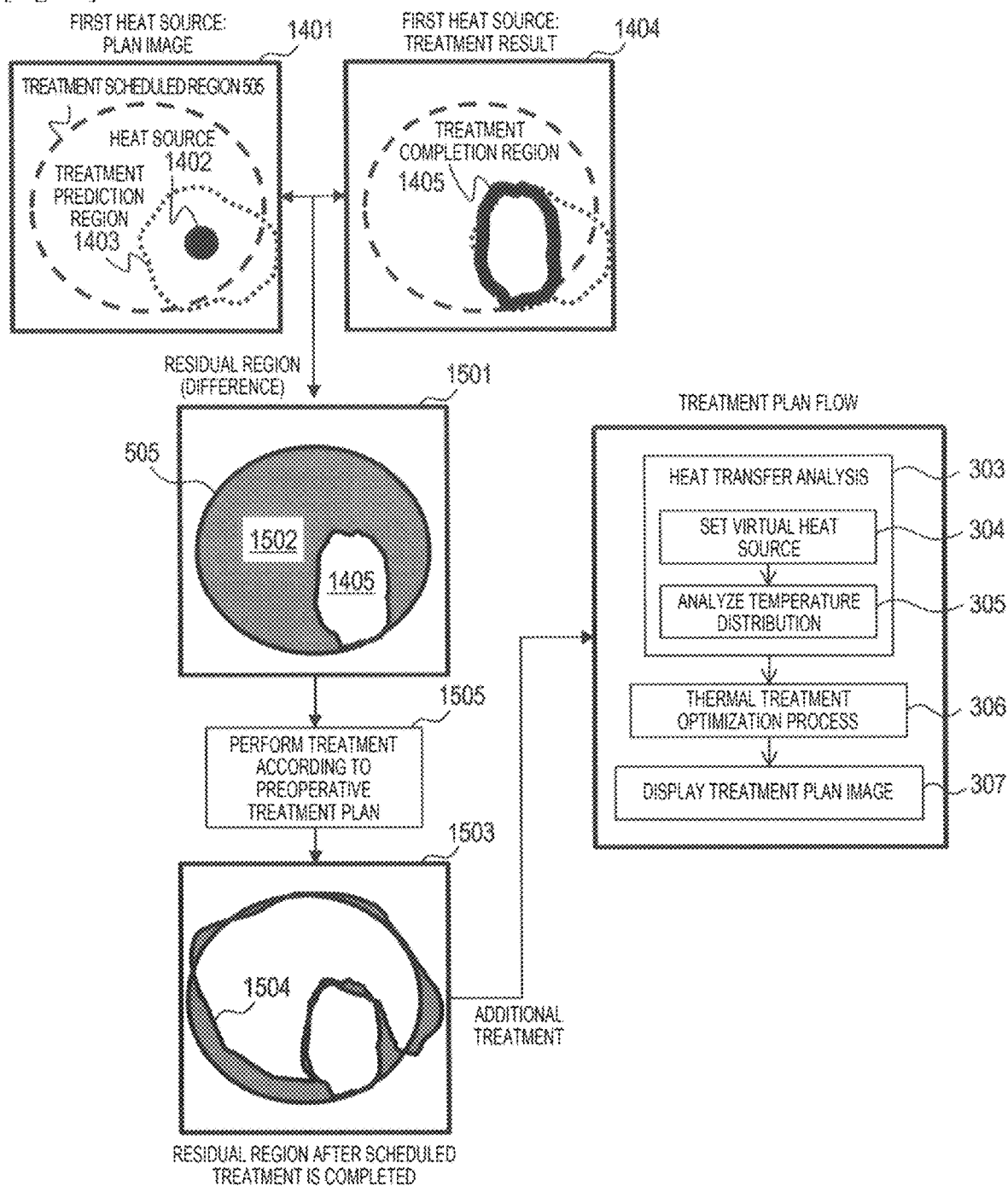

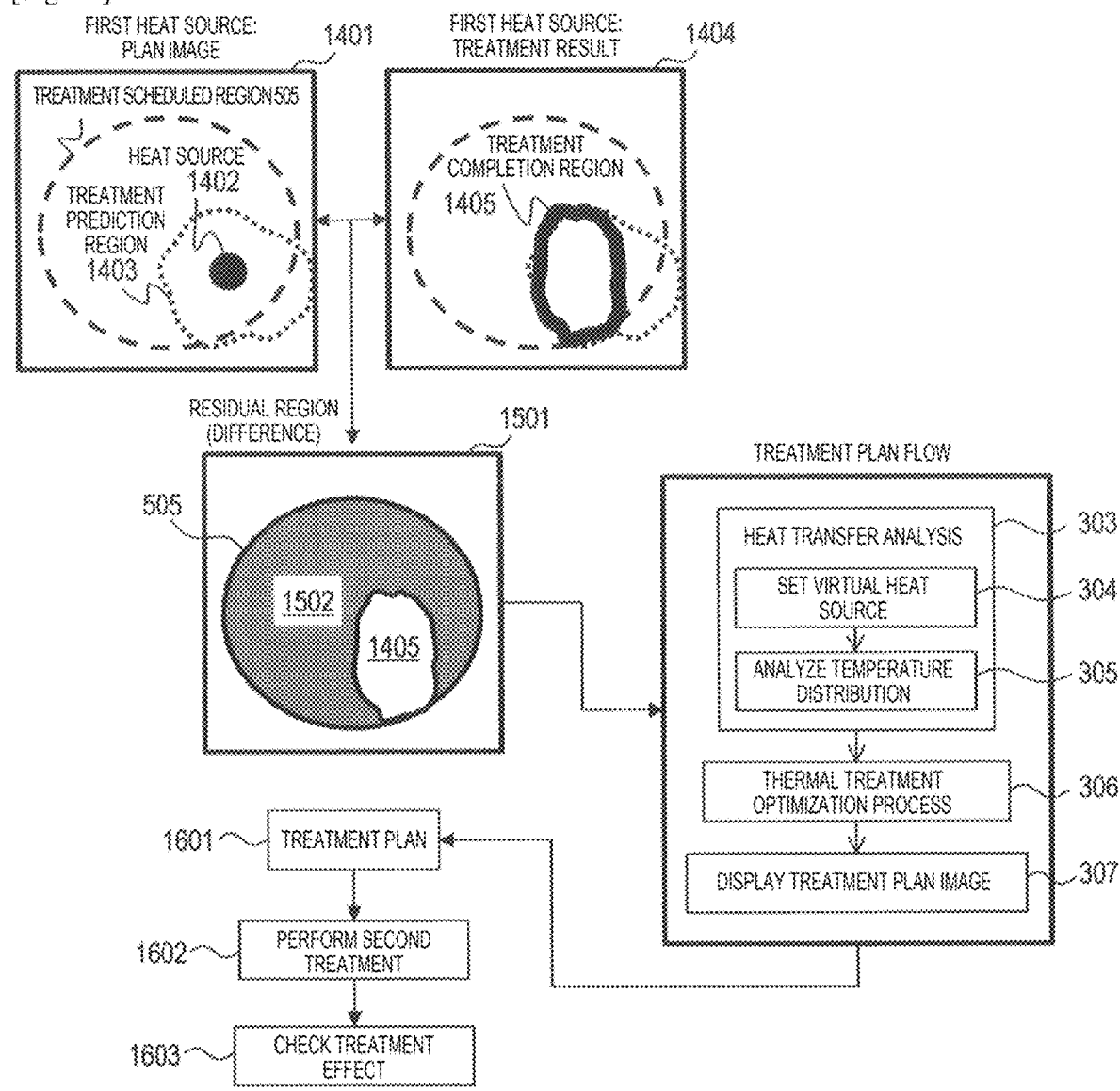

US 10,667,866 B2

TREATMENT SUPPORT APPARATUS AND TREATMENT SUPPORT METHOD

CLAIM OF PRIORITY

The present application claims priority from Japanese patent application JP 2017-114910 filed on Jun. 12, 2017, the content of which is hereby incorporated by reference into this application.

TECHNICAL FIELD

The present invention relates to a technology for supporting thermal treatment.

BACKGROUND ART

A medical image display apparatus typified by an ultrasonic wave, magnetic resonance imaging (MM), and X-ray computed tomography (CT) is an apparatus which provides invisible internal information of a living body in a form of a numerical value or an image, and is widely used. A contrast agent is mainly used for imaging of a blood vessel, microbubbles (fine bubbles) are used for contrast-enhanced US (CEUS), a gadolinium contrast agent is used for MR angiography (MRA), and an iodine contrast agent is used for CT angiography (CTA). A high resolution of an ultrasonic wave has been realized to draw a fine blood vessel of 0.1 mm order such as a tumorous blood vessel or an inflammatory blood vessel with the advance of the recent technology for high-speed transmission and reception and high-speed computation in a non-contrast blood vessel imaging technology based on correlation calculation. A tumorous blood vessel is abnormal in a distribution or a shape compared with normal tissue, and is an important observation target in tumor diagnosis. Therefore, in an image diagnosis apparatus, in addition to improvement of image quality through high resolution and high sensitivity of blood vessel drawing, technology development for evaluating functional property such as tissue property and states of blood flow dynamics is progressing.

On the other hand, regarding a treatment technology, minimally invasive treatment in which a hospitalization period is short and postoperative progress is also favorable has become widespread, and is also being expanded to adaptive diseases. There are many types of minimally invasive treatments, and, for example, there is laparoscopic surgery in which surgery is performed under an endoscope inserted into a hole of about 2 cm in a body surface part, or a thermal treatment technology of thermally necrosing an affected part. Various methods are proposed regarding the thermal treatment, and adaptive diseases are different from each other. For example, in radio frequency ablation (RFA), a needle with an electrode at the tip thereof punctures an affected part, and a region with a radius of about 10 mm is heated at about 70 degrees such that tissue is thermally necrosed. This is mainly applied to liver cancer, and an incision is smaller, and bleeding is less than in abdominal surgery, so that a physical damage of a patient is considerably small. Microwave ablation (MWA) using microwaves, Cryo which is cooling treatment, and high intensity focused ultrasound (HIFU) in which a heating region is formed by using high-intensity focused ultrasound such that tissue is solidified, are clinically used. Since an affected part cannot be directly observed in the minimally invasive treatment, it is necessary to recognize an affected part, a positional relationship of peripheral tissues, or a distribution of blood vessels or nerves in advance, and thus preoperative simulation is focused.

PTL 1 discloses preoperative simulation of a patient specific temperature distribution in organs, due to an ablation device. In this simulation, a blood vessel structure of a patient is extracted from a medical image, and heat transfer is estimated by taking into consideration a heat sink effect in a blood vessel. Temperature maps are generated to display the effects of ablation according to different ablation currents and ablation device positions, and a more appropriate position of the ablation device is determined on the basis thereof.

CITATION LIST

Patent Literature

PTL 1: US 2014/0296842 A1

SUMMARY OF INVENTION

Technical Problem

Problems of thermally minimally invasive treatment are that it is hard to predict a temperature distribution caused by heating, and optimization of arrangement of heat sources is difficult. A main factor thereof is heat convection (heat sink effect) due to a blood flow. Heat transfer is roughly classified into thermal conduction in which heat is mainly transferred from a high temperature part to a low temperature part in tissue, and heat convection corresponding to heat movement due to a temperature gradient inside a fluid (blood flow). A tissue structure of tumor is actually considerably complex, but a temperature distribution can be predicted to some degree through simple modeling by disregarding symmetry or a difference in thermal conductivity in living body tissue. However, a blood vessel structure has a width of 1 mm to 0.1 mm, receives differing influence of heat convection depending on blood vessel density or tortuousness, and is thus more greatly influenced than by thermal conduction. Thus, heating deficiency occurs in the vicinity of a blood vessel, and this causes recurrence risk. In order to prevent this, a region which is 10 mm or more wider than tumor is set as a margin region, and treatment is performed.

In the technology disclosed in PTL 1, a blood vessel is extracted from a medical image, and heat transfer estimation is performed by taking into consideration the heat sink effect. A result of the heat transfer estimation is displayed as a temperature map, and an operator makes a preoperative plan for heat source arrangement by referring to the display result.

However, a problem remains in terms of optimization in a case where a plurality of heat sources are disposed, particularly, optimization in a case where treatment progresses stepwise. In other words, tissue denaturation due to first treatment influences heat convection due to a loss of a blood vessel, and is thus required to be included in optimization of heat source arrangement in second treatment. In other words, as a function required for a treatment simulator for thermally minimally invasive treatment, a function of optimizing an order of treatment along with arrangement of heat sources and supporting a preoperative plan until treatment completion is necessary.

In consideration of the above circumstances, an object of the invention is to support thermal treatment through a function of presenting a treatment plan in which a position of a heat source and a treatment order are optimized in the field of thermally minimally invasive treatment.

Solution to Problem

Therefore, according to the invention, there is provided a treatment support apparatus including a processor; and a storage device connected to the processor, in which the storage device holds image information of tissue in a living body of a treatment target, and in which the processor extracts a blood vessel structure of the inside of the living body from the image information, calculates positions of one or more heat sources for thermal treatment on a treatment scheduled region including at least a part of the extracted blood vessel structure on the basis of the extracted blood vessel structure, and outputs data for displaying an image including the calculated positions of the one or more heat sources.

Advantageous Effects of Invention

According to the invention, thermally minimally invasive treatment is realized in which treatment is completed with higher accuracy and within a shorter period of time than in the related art. As a result, effects of reducing a hospitalization period, preventing recurrence, and reducing an operation time can be expected, and thus physical burdens and economic burdens on both of an operator and a patient are reduced. Objects, configurations, and effects other than those described above will become apparent through description of the following embodiment.

BRIEF DESCRIPTION OF DRAWINGS

FIG. 1 is a block diagram illustrating a configuration of a treatment support apparatus according to an embodiment of the invention.

FIG. 2 is an explanatory diagram illustrating a flow of treatment using the treatment support apparatus according to the embodiment of the invention.

FIG. 3 is a flowchart illustrating a process performed by the treatment support apparatus according to the embodiment of the invention.

FIG. 4 is an explanatory diagram illustrating heat transfer analysis performed by the treatment support apparatus according to the embodiment of the invention.

FIG. 5 is an explanatory diagram illustrating a blood vessel image and a blood vessel analysis image acquired by the treatment support apparatus according to the embodiment of the invention.

FIG. 6 is an explanatory diagram illustrating heat transfer analysis performed by the treatment support apparatus according to the embodiment of the invention.

FIG. 7 is an explanatory diagram illustrating a thermal treatment optimization process performed by the treatment support apparatus according to the embodiment of the invention.

FIG. 8 is an explanatory diagram illustrating a treatment plan creation process performed by the treatment support apparatus according to the embodiment of the invention.

FIG. 9 is a flowchart illustrating details of the thermal treatment optimization process performed by the treatment support apparatus according to the embodiment of the invention.

FIG. 10 is an explanatory diagram illustrating a first example of the thermal treatment optimization process performed by the treatment support apparatus according to the embodiment of the invention.

FIG. 11 is an explanatory diagram illustrating a second example of the thermal treatment optimization process performed by the treatment support apparatus according to the embodiment of the invention.

FIG. 12 is an explanatory diagram illustrating a third example of the thermal treatment optimization process performed by the treatment support apparatus according to the embodiment of the invention.

FIG. 13 is a flowchart illustrating an intraoperative process performed after an operator of the treatment support apparatus according to the embodiment of the invention starts treatment.

FIG. 14 is an explanatory diagram illustrating an intraoperative process using the treatment support apparatus according to the embodiment of the invention.

FIG. 15 is an explanatory diagram illustrating a first example of the intraoperative process using the treatment support apparatus according to the embodiment of the invention.

FIG. 16 is an explanatory diagram illustrating a second example of the intraoperative process using the treatment support apparatus according to the embodiment of the invention.

DESCRIPTION OF EMBODIMENTS

An embodiment of the invention will be described with reference to the drawings.

FIG. 1 is a block diagram illustrating a configuration of a treatment support apparatus 100 of the invention.

The treatment support apparatus 100 includes a control processor 101, a memory 102, and a transmission/reception control unit 107. The control processor 101 performs various processes for realizing a function of the treatment support apparatus 100 according to a program stored in the memory 102. The memory 102 is a storage device such as a dynamic random access memory (DRAM), and stores software such as a program executed by the control processor 101, data referred to when the control processor 101 executes the program, and data generated as a result of the control processor 101 executing the program. For example, the memory 102 stores an image generation processing unit 103, a blood flow measurement processing unit 104, a heat transfer estimation processing unit 105, and a heat source arrangement optimization processing unit 106.

In the example illustrated in FIG. 1, the processing units are realized by the control processor 101 executing the software stored in the memory 102. Therefore, in the following description, processes performed by the processing units are actually performed by the control processor 101. However, the processing units may function as hardware by incorporating the software for realizing the processing units into a field programmable gate array (FPGA) or an application specific integrated circuit (ASIC).

Details of processes performed by the processing units will be described later.

The transmission/reception control unit 107 is connected to a probe 110, and includes a transmission beam former 108 and a reception beam former 109 in order to control transmission and reception of signals with the probe 110. The transmission beam former 108 controls a voltage, a timing, and duration of an electric signal which is input to a plurality of piezoelectric elements (not illustrated) forming the probe 110.

An electric signal which is given delay time by the transmission beam former 108 and is input to the probe 110 is converted into an acoustic signal (ultrasonic wave) by the piezoelectric element so as to be transmitted to an examination target 111. The acoustic signal reflected in the middle of propagating through the examination target 111 is received by the probe 110 again, and is then converted into an electric signal by the piezoelectric element so as to be input to the reception beam former 109.

The reception beam former 109 returns a phase corresponding to the delay time given by the transmission beam former 108, and performs an addition process (phasing addition). The electric signal having undergone the phasing addition is a complex RF signal, and is a constituent element of a vertical line of a finally constructed image.

The control processor 101 reads the software stored in the memory 102 as described above, performs signal processing using an RF signal, and then sends a numerical value or an image as a result thereof to a display unit 130. Specifically, the image generation processing unit 103 converts the amplitude of the RF signal into luminance information, so as to generate image information indicating a shape of tissue. The image generation processing unit 103 at least temporarily stores the generated image information in the memory 102, and transmits the image information to the display unit 130 in order to display an image as necessary.

The treatment support apparatus 100 is connected to an external input device 120 and the display unit 130. The external input device 120 is an input device such as a keyboard, a mouse, or a touch panel, and information is input to the control processor 101 via the external input device. The display unit 130 is an output device such as a liquid crystal panel, and a result of a process performed by the control processor 101 is output via the display unit.

FIG. 1 illustrates an example in which the treatment support apparatus 100 is realized by using an ultrasonic diagnosis apparatus. For example, hardware such as the control processor 101, the memory 102, and the transmission/reception control unit 107 is the same as that of an ultrasonic diagnosis apparatus of the related art, and the treatment support apparatus 100 of the present embodiment may be realized by adding the software for realizing the image generation processing unit 103 to the heat source arrangement optimization processing unit 106 of the present embodiment to the memory 102. FIG. 1 illustrates that the probe 110, the external input device 120, and the display unit 130 are connected to the treatment support apparatus 100, but the whole including the devices may be referred to as a treatment support apparatus. However, the above-described configuration is only an example, and the treatment support apparatus 100 may be realized by using other types of diagnosis apparatuses such as an MM apparatus or an X-ray CT apparatus as long as an image of tissue such as a blood vessel in a living body which is a treatment target can be acquired.

FIG. 2 is an explanatory diagram illustrating a flow of treatment using the treatment support apparatus 100 according to the embodiment of the invention.

First, an operator 220 starts imaging using the probe 110 (step 201). In the treatment support apparatus 100, the probe 110 transmits an ultrasonic wave to the examination target 111 and receives an ultrasonic wave reflected from the examination target 111 (step 202), and the image generation processing unit 103 generates an image of a blood vessel in the examination target 111 on the basis of the received signal and stores the image in the memory 102 (step 203). In a case where the blood flow measurement processing unit 104, the heat transfer estimation processing unit 105, and the heat source arrangement optimization processing unit 106 generate and output data regarding a treatment plan image on the basis of the image of the blood vessel, the display unit 130 displays the treatment plan image on the basis of the data (step 204). The displayed treatment plan image includes an image displaying recommended heat source arrangement as will be described later (refer to FIG. 8).

The operator 220 creates a preoperative treatment plan by referring to the displayed treatment plan image (step 305). For example, the operator 220 may take into consideration a risk or the like in a case where treatment is actually performed according to the recommended heat source arrangement by referring to the displayed treatment plan image, and then determine heat source arrangement in actual treatment. The operator starts first treatment according to the created preoperative treatment plan (step 206). Specifically, the thermal treatment on positions of heat sources for the first treatment determined in the preoperative treatment plan by using a treatment device 221 is performed (step 207). The thermal treatment is roughly classified into puncture treatment (for example, RFA or cryo) in which a treatment device for heating or cooling punctures an affected part and irradiation treatment (for example, HIFU) in which radiation or a strong ultrasonic wave is applied (remotely), but either treatment may be performed. Since arrangement of heat sources greatly influences the accuracy of treatment in either case, as a treatment plan, arrangement (that is, a position of each heat source) of one or more heat sources and an order of heating or cooling the heat sources are determined. In the following description, an example of heating will be described, but the same process may be performed for cooling, and, thus, the present embodiment is applicable to any thermal treatment as necessary.

In a case where the operator 220 determines that the first treatment is completed (step 208), the probe 110 transmits an ultrasonic wave to the examination target 111 and receives an ultrasonic wave reflected from the examination target 111 (step 209), the image generation processing unit 103 generates an image of a blood vessel in the examination target 111 on the basis of the received signal (step 210), the blood flow measurement processing unit 104, the heat transfer estimation processing unit 105, and the heat source arrangement optimization processing unit 106 generate a treatment plan image, and the display unit 130 displays the generated treatment plan image (step 211). Steps 209 to 211 are performed in the same manner as the above steps 202 to 204. Details of steps 203, 204, 210 and 211 will be described later with reference to FIG. 3 and the like.

The operator 220 refers to the displayed treatment plan image so as to make a retreatment plan (step 212). Specifically, the operator 220 refers to the displayed treatment plan image so as to check a region of which treatment is actually completed through the first treatment, and determines heat source arrangement for second treatment in a case where a region of which treatment is not completed remains in a treatment scheduled range. It is determined whether or not treatment of the entire treatment scheduled range is completed (that is, a region of which treatment is not completed remains in the treatment scheduled range) (step 213), the second treatment is started according to the heat source arrangement determined in step 212 (step 214) in a case where the treatment is not completed (step 213: No), and the treatment is finished (step 215) in a case where the treatment is completed (step 215: Yes). In a case where the second treatment is started in step 214, then, the same processes in step 207 and the subsequent steps are repeatedly performed.

FIG. 3 is a flowchart illustrating a process performed by the treatment support apparatus 100 according to the embodiment of the invention.

First, the image generation processing unit 103 generates a blood vessel image (step 301). This step corresponds to step 203 in FIG. 2. In the present embodiment, the probe 110 transmits an ultrasonic wave and receives a reflected wave from the examination target 111, and the image generation processing unit 103 generates the blood vessel image through well-known image processing. For example, any method may be used as long as an image in which a blood vessel distribution can be specifically displayed in an emphasis manner, such as a contrast agent image using an ultrasonic contrast agent or a Doppler image, can be obtained.

Next, the blood flow measurement processing unit 104 performs blood vessel analysis (step 302). Specifically, the blood flow measurement processing unit 104 calculates a distribution (density and the magnitude of a blood vessel diameter) of a blood vessel, a shape (for example, tortuousness and branch) thereof, and a flow rate as numerical value information.

Next, the heat transfer estimation processing unit 105 performs heat transfer analysis (step 303). Specifically, the heat transfer estimation processing unit 105 calculates a temperature distribution on the basis of a result of the blood vessel analysis in step 302 and the set heat source position. In the following description, a heat source of which a position, a heat amount, and the like are assumed in order to compute heat transfer analysis before actual treatment is performed will also be referred to as a virtual heat source. Heat transfer is roughly classified into thermal conduction in which heat is transferred in tissue, and heat convection corresponding to heat movement (heat sink effect) by a fluid (here, a blood flow). The heat transfer estimation processing unit 105 of the present embodiment sets a position and a heat amount of a virtual heat source (step 304), and analyzes a temperature distribution by receiving such information and the result of the blood vessel analysis (step 305).

Next, the heat source arrangement optimization processing unit 106 performs a thermal treatment optimization process of analyzing optimal heat source arrangement on the basis of the result of the heat transfer analysis (step 306). Here, the optimal heat source arrangement is, for example, the arrangement of heat sources in which treatment of the entire treatment scheduled region (which will be described later) can be completed with the minimum number of heat sources. The heat source arrangement optimization processing unit 106 outputs the result via the display unit 130 (step 307). For example, the heat source arrangement optimization processing unit 106 generates data for displaying an image displaying a blood vessel structure, the determined arrangement of the heat sources, and the like, and outputs the data to the display unit 130, and the display unit 130 displays the image. An example of a displayed image will be described later with reference to FIG. 8.

FIG. 4 is an explanatory diagram illustrating heat transfer analysis performed by the treatment support apparatus 100 according to the embodiment of the invention.

Specifically, FIG. 4 illustrates an example of the virtual heat source setting (step 304). For example, the heat transfer estimation processing unit 105 may predict the influence of heat convection on the basis of the blood vessel analysis result (step 401), and may set a position where the heat convection is strong as a position of a heat source on the basis of the result (step 402). The position where heat convection is strong is a position where the influence of the heat sink effect is strongly shown, for example, the vicinity of a thick blood vessel in which a flow rate is high. It may be considered that, since a blood vessel is caused to disappear by treating such a position at first, the influence of the heat sink effect in the subsequent treatment is reduced, and thus the efficiency of treatment is improved. In step 401, the heat transfer estimation processing unit 105 may exclude a minute blood vessel which is distributed in low density from a computation target. Consequently, the accuracy of computation is reduced, but computation resources and computation time can be saved.

Alternatively, the heat transfer estimation processing unit 105 may set the center of a treatment scheduled region as a position of a heat source (step 403), and may set a position which is input by the operator using the external input device 120 as a position of a heat source (step 404).

A processing (step 305) of analyzing a temperature distribution on the basis of the position of the heat source set in step 302 and the heat amount may be performed according to a well-known method. As an example, the heat transfer estimation processing unit 105 may perform heat transfer analysis according to the following fundamental equations. Equation (1) is used for computation of thermal conduction, and Equation (2) is used for computation of heat convection.

Equation for thermal conduction:

$$Q = qA = -\lambda \frac{dT}{dx} A \quad (1)$$

Equation for heat convection: $Q = qA = h(T_f - T_s)A$  (2)

Q: a heat transfer amount
q: heat flux
A: a sectional area
$\lambda$: heat conductivity
h: a heat transfer rate
T: a temperature
$T_f$: a fluid (blood flow) temperature
$T_s$: a solid (tissue) temperature Next, details of the processes illustrated in FIGS. 2 to 4 will be described by using specific examples.

FIG. 5 is an explanatory diagram illustrating a blood vessel image and a blood vessel analysis image acquired by the treatment support apparatus 100 according to the embodiment of the invention.

FIG. 5(A) illustrates an example of a blood vessel image 501 generated in step 301. The blood vessel image 501 includes, for example, a tumor region 502, and blood vessels 503 in and on the periphery of the tumor region 502.

FIG. 5(B) illustrates an example of a blood vessel analysis image 504 in the blood vessel analysis performed in step 302. The blood flow measurement processing unit 104 calculates a distribution of blood vessels, shapes of the blood vessels, a flow rate, an abnormal blood vessel, and the like. The abnormal blood vessel may be automatically extracted according to a statistical method on the basis of information regarding the distribution and the shapes of the blood vessels. A treatment scheduled region 505 is set to include the tumor region 502 on the basis of the result of the blood vessel analysis.

The treatment scheduled region 505 may be set according to various methods. For example, by using the tendency that a tumorous blood vessel easily meanders, the treatment scheduled region 505 including the tumor region 502 may be automatically set on the basis of information regarding tortuousness of a blood vessel included in a treatment scheduled region blood vessel analysis result. Alternatively, the treatment scheduled region 505 including the tumor region 502 may be automatically set on the basis of a luminance difference between the tumor region 502 and other regions in an image. Alternatively, the display unit 130 may display a blood vessel analysis image, the operator may refer to the image, and operate the external input device 120 so as to manually set the treatment scheduled region 505 including the tumor region 502.

FIG. 6 is an explanatory diagram illustrating the heat transfer analysis performed by the treatment support apparatus 100 according to the embodiment of the invention.

FIG. 6 illustrates an example of a result of performing heat transfer analysis according to methods as shown in Equations (1) and (2) by setting a heat source position in a case where the blood vessel analysis result as illustrated in FIG. 5(B) is obtained. Here, FIG. 6 illustrates two examples in which set heat source positions are different from each other as temperature distribution images 601 and 603. In these examples, as a result of thermal treatment, ranges of temperatures of 30° C. or more and below 50° C., 50° C. or more and below 70° C., and 70° C. or more which are predicted through the heat transfer analysis are displayed. Herein, an example in which ablation (that is, heating) is performed as thermal treatment is described, but cooling may be performed as thermal treatment, and, in this case, a range in which a temperature is predicted to be reduced is displayed.

In the example of the blood vessel analysis image illustrated in FIG. 5(B), a blood vessel density in the treatment scheduled region is high in the right region in the image, and is low in the left region. Thus, as shown in the temperature distribution image 601, in a case where a heat source 602 is set centering on the treatment scheduled region, heat convection more strongly occurs in the right region (that is, due to the heat sink effect), and thus a temperature increase is suppressed. In contrast, in the left region, the influence of the heat sink effect is small, and thus a temperature increases in a wide range.

On the other hand, as shown in the temperature distribution image 603, in a case where a heat source 604 is set in the right region in which a blood vessel density is high, asymmetry of a range in which a temperature increases is reduced, but a treatment region (that is, a region in which a temperature increases to a predetermined value or greater) is reduced due to the heat sink effect.

FIG. 7 is an explanatory diagram illustrating the thermal treatment optimization process performed by the treatment support apparatus 100 according to the embodiment of the invention.

FIG. 7 illustrates examples of details of the thermal treatment optimization process performed in step 306, that is, a flow of treatment simulation in a case where the blood vessel analysis result illustrated in FIG. 5(B) is obtained.

A temperature distribution image 701 indicates an example of setting a first heat source 702 and performing first heat transfer analysis. The treatment support apparatus 100 builds the temperature distribution image 701 on the basis of the blood vessel analysis image 504 according to the same method as described with reference to FIG. 6, and predicts a treatment completion region obtained through first thermal treatment on the basis thereof. Here, the treatment completion region is a region in which a temperature increases to a predetermined temperature (for example, 50° C.) or higher which is necessary for treatment as a result of the thermal treatment. In the following description, a treatment completion region which is predicted through heat transfer analysis will be referred to as a treatment prediction region.

A treatment prediction region 704 in the first thermal treatment is displayed in a blood vessel analysis image 703. In blood vessels included in the treatment completion region, a blood flow is almost blocked due to tissue denaturation, and thus the heat sink effect is reduced. The treatment support apparatus 100 determines second heat source arrangement on the basis of a blood vessel distribution image excluding a blood vessel included in a treatment prediction region 704 among blood vessels included in the blood vessel analysis image 504 before treatment, and performs second heat transfer analysis. A temperature distribution image 705 indicates an example of a result of the second heat transfer analysis. In this example, a range in which a temperature increases in a case where a heat source 706 is set is displayed. As described above, the accuracy of a treatment prediction region is improved by performing the next and subsequent heat transfer analysis on the basis of a blood vessel structure which is predicted to change due to treatment until the previous time.

The treatment support apparatus 100 determines optimal heat source arrangement by repeatedly performing the above-described processes as necessary. An example thereof will be described with reference to FIG. 8.

FIG. 8 is an explanatory diagram illustrating a treatment plan creation process performed by the treatment support apparatus 100 according to the embodiment of the invention.

FIG. 8 illustrates examples of treatment plan images in which respective positions of heat sources in thermal treatment performed a plurality of times, an order of the plurality of times of thermal treatment, treatment completion regions predicted as results of the plurality of times of thermal treatment, and the like are displayed by using the result of the thermal treatment optimization process described with reference to FIG. 7.

Specifically, a temperature distribution image 801 displays a heat source 802 set for the first time, and a treatment prediction region 803 obtained through first heat transfer analysis based on the heat source 802. A temperature distribution image 804 displays a heat source 805 set for the second time, and a treatment prediction region 806 obtained through second heat transfer analysis based on the heat source 805. A temperature distribution image 807 displays a heat source 808 set for the third time, and a treatment prediction region 809 obtained through third heat transfer analysis based on the heat source 808.

A temperature distribution image 810 is an image obtained by overlapping the heat sources and the treatment prediction regions corresponding to the three times.

A treatment prediction image 811 displays a treatment prediction region 812 which is the union (that is, a set of regions included in at least any of the treatment prediction region 803, the treatment prediction region 806, and the treatment prediction region 809) of the treatment prediction regions corresponding to the three times. The treatment prediction region is a region of which treatment is predicted to be completed through the three times of thermal treatment. In the example illustrated in FIG. 8, the substantially entire treatment scheduled region 505 and the entire tumor region 502 are included in the treatment prediction region 812.

The treatment support apparatus 100 displays the images 801, 804, 807, 810 and 811 illustrated in FIG. 8, and can thus provide information regarding one or more positions of heat sources and an order of thermal treatment on the heat sources. FIG. 8 illustrates an example in which treatment of the entire treatment scheduled region 505 is predicted to be completed through three times of treatment, but, in a case where treatment of the entire treatment scheduled region 505 is predicted to be completed through one time of treatment, a position of a heat source in the one time of treatment may be displayed, and information regarding an order is not necessary.

Determination of positions of heat sources, determination of an order, and determination of finishing of a plurality of times of thermal treatment in the thermal treatment optimization process described with reference to FIGS. 7 and 8 may be performed according to various methods. Some examples thereof will now be described.

FIG. 9 is a flowchart illustrating details of the thermal treatment optimization process performed by the treatment support apparatus 100 according to the embodiment of the invention.

First, the heat source arrangement optimization processing unit 106 sets a treatment scheduled region (step 901). Specifically, as described with reference to FIG. 5, a treatment scheduled region may be automatically set, and a treatment scheduled region may be set according to information which is input by the operator.

Next, the heat source arrangement optimization processing unit 106 determines a position of a heat source (step 902). For example, the heat source arrangement optimization processing unit 106 may preferentially determine a position of a heat source where ablation can be performed in the widest range, may determine a position of a heat source such that ablation is performed in order from an end, and may preferentially determine a position where a heat progress effect is high as a position of a heat source. Specific examples of determination methods will be described later (refer to FIGS. 10 to 12).

Next, the heat source arrangement optimization processing unit 106 predicts a treatment completion region in a case where treatment is performed on the heat source determined in step 902 (step 903). Specifically, the heat source arrangement optimization processing unit 106 may call the heat transfer estimation processing unit 105, and may predict a treatment completion region by the heat transfer estimation processing unit 105 performing heat transfer analysis in a case where a predetermined heat amount is applied to the position of the heat source determined in step 902.

Next, the heat source arrangement optimization processing unit 106 performs spatial analysis on the treatment scheduled region set in step 901 and the treatment completion region predicted in step 903 (step 904). Specifically, the heat source arrangement optimization processing unit 106 analyzes a region of which treatment is predicted to be completed in the treatment hitherto, a treatment scheduled region, and a positional relationship of a blood vessel or the like in the treatment scheduled region.

Next, the heat source arrangement optimization processing unit 106 determines whether or not treatment of the treatment scheduled region is completed (step 905). For example, the heat source arrangement optimization processing unit 106 may determine that treatment is completed in a case where the entire treatment scheduled region set in step 901 overlaps the predicted treatment completion region, and may determine that treatment is completed in a case where the number of set heat sources reaches a predetermined upper limit. By performing the former determination, it is possible to dispose a heat source which enables reliable treatment to be performed while reducing burdens on an operator and a patient. However, for example, in a case where the number of times of treatment is restricted by a position of a treatment scheduled region or a condition of the periphery thereof, the latter determination may be performed. According thereto, heat source arrangement is realized in which a treatment effect is highest within a restricted number of times of treatment.

In a case where it is determined that treatment is not completed in step 905 (step 905: No), the process returns to step 902. The heat source arrangement optimization processing unit 106 determines a position of the next heat source such that a size of an overlapping portion between a predicted treatment completion region and a treatment scheduled region is increased. The processes are repeatedly performed until treatment is completed in step 905. In step 903 performed for the second and subsequent times, the heat source arrangement optimization processing unit 106 may predict a change in a blood vessel structure in a case where thermal treatment is performed on heat sources set until the previous time, and may predict a treatment completion region through heat transfer analysis based thereon. Consequently, it is possible to calculate a position of a heat source for reliably treating a treatment scheduled region.

In a case where it is determined that treatment is completed in step 905 (step 905: Yes), the thermal treatment optimization process is finished (step 906), and all of positions of the heat sources set in step 902 and an order thereof are output.

FIG. 10 is an explanatory diagram illustrating a first example of the thermal treatment optimization process performed by the treatment support apparatus 100 according to the embodiment of the invention.

In the first example illustrated in FIG. 10, a position of a heat source enabling ablation to be performed in the widest range is preferentially determined. In a case where the influence of the heat sink effect is small, this method is efficient.

An image 1001 in FIG. 10(A) displays, for example, the treatment scheduled region 505 set in step 901 by the heat source arrangement optimization processing unit 106, a heat source 1002 in the first treatment determined in step 902 performed for the first time, and a treatment prediction region 1003 indicating a result predicted in step 903 performed for the first time. In the first example, the heat source arrangement optimization processing unit 106 preferentially determines a position of a heat source which enables ablation to be performed in the widest range. However, in the example illustrated in FIG. 10(A), a position (that is, an initial value) of the first heat source 1002 is determined centering on the treatment scheduled region 505.

An image 1004 in FIG. 10(B) displays a treatment completion region 1005 specified on the basis of a result of step 903 performed for the first time. This is the same as the treatment prediction region 1003. The heat source arrangement optimization processing unit 106 analyzes a positional relationship among the treatment scheduled region 505, the treatment completion region 1005, and the blood vessels 503 in step 904 performed for the first time.

As displayed in the image 1004, in a case where there is a region which is included in the treatment scheduled region 505 but is not included in the treatment completion region 1005, it is determined that treatment is not completed in step 905 (step 905: No). In this case, the process returns to step 902, and a position of the next heat source is determined. An image 1006 in FIG. 10(C) displays, for example, a heat source 1007 in the second treatment determined in step 902 performed for the second time by the heat source arrangement optimization processing unit 106, and a treatment prediction region 1008 indicating a result predicted in step 903 performed for the second time.

The heat source arrangement optimization processing unit 106 in the first example may set a heat source therein so as to determine a position where ablation can be predicted to be performed most broadly on a region not included in the treatment completion region 1005 yet in the treatment scheduled region 505 as a position of the heat source 1007. In a case where this prediction is performed, the heat source arrangement optimization processing unit 106 may or may not take into consideration the heat sink effect on the basis of arrangement or the like of blood vessels (which is kept not undergoing ablation even if treatment is performed as predicted) not included in the treatment completion region 1005 until the previous time.

The heat source arrangement optimization processing unit 106 sets the union between the treatment completion region 1005 indicating a result of prediction until the previous time and a treatment prediction region 1008 obtained through the present prediction, as the new treatment completion region 1005. The heat source arrangement optimization processing unit 106 analyzes a positional relationship among the new treatment completion region 1005, the treatment scheduled region 505, and the blood vessels 503 in step 904 performed for the second time.

FIG. 11 is an explanatory diagram illustrating a second example of the thermal treatment optimization process performed by the treatment support apparatus 100 according to the embodiment of the invention.

In the second example, simply, a position of a heat source is determined such that treatment progresses in order from an end of a treatment scheduled region.

An image 1101 in FIG. 11(A) displays, for example, the treatment scheduled region 505 set in step 901 by the heat source arrangement optimization processing unit 106, a heat source 1102 in the first treatment determined in step 902 performed for the first time, and a treatment prediction region 1103 indicating a result predicted in step 903 performed for the first time. In the second example, the heat source arrangement optimization processing unit 106 determines a position of a heat source such that ablation is performed in order from an end of the treatment scheduled region 505. However, the first heat source 1102 may be set at any position in the treatment scheduled region 505.

An image 1104 in FIG. 11(B) displays a treatment completion region 1105 specified on the basis of a result of step 903 performed for the first time. This is the same as the treatment prediction region 1103. The heat source arrangement optimization processing unit 106 analyzes a positional relationship among the treatment scheduled region 505, the treatment completion region 1105, and the blood vessels 503 in step 904 performed for the first time.

As displayed in the image 1104, in a case where there is a region which is included in the treatment scheduled region 505 but is not included in the treatment completion region 1105, it is determined that treatment is not completed in step 905 (step 905: No). In this case, the process returns to step 902, and a position of the next heat source is determined. An image 1106 in FIG. 11(C) displays, for example, a heat source 1107 in the second treatment determined in step 902 performed for the second time by the heat source arrangement optimization processing unit 106, and a treatment prediction region 1108 indicating a result predicted in step 903 performed for the second time.

The heat source arrangement optimization processing unit 106 in the second example may determine a position of the heat source 1107 such that a boundary of a treatment prediction region, when the position is set as a heat source, comes close to a boundary of a residual region (that is, a region which does not overlap any treatment prediction region in the treatment scheduled region 505). Specifically, for example, the heat source arrangement optimization processing unit 106 in the second example may determine a position of any point included in the treatment scheduled region 505 or a position in the vicinity thereof among points on a boundary of the treatment completion region 1105 at that time, as a point of the heat source 1107.

The heat source arrangement optimization processing unit 106 sets the union between the treatment completion region 1105 indicating a result of prediction until the previous time and a treatment prediction region 1108 obtained through the present prediction, as the new treatment completion region 1105. The heat source arrangement optimization processing unit 106 analyzes a positional relationship among the new treatment completion region 1105, the treatment scheduled region 505, and the blood vessels 503 in step 904 performed for the second time.

According to the second example, since a heat transfer effect including the heat sink effect is not taken into consideration when a position of a heat source is determined, it is possible to create a treatment plan to certainly complete treatment of a treatment scheduled region while reducing a computation source.

FIG. 12 is an explanatory diagram illustrating a third example of the thermal treatment optimization process performed by the treatment support apparatus 100 according to the embodiment of the invention.

In the third example, a position of a heat source is determined by taking into consideration the heat sink effect.

An image 1201 in FIG. 12(A) displays, for example, the treatment scheduled region 505 set in step 901 by the heat source arrangement optimization processing unit 106, a heat source 1202 in the first treatment determined in step 902 performed for the first time, and a treatment prediction region 1203 indicating a result predicted in step 903 performed for the first time. In the third example, the heat source arrangement optimization processing unit 106 preferentially sets a heat source at a position where the heat sink effect is considerable in the treatment scheduled region 505. Specifically, the heat source arrangement optimization processing unit 106 may preferentially set a heat source at a position where a blood vessel density is high, and may preferentially employ a position of a heat source in which a temperature increase range is narrow by performing the heat transfer analysis as illustrated in FIG. 6 on positions of a plurality of heat sources in the treatment scheduled region 505.

An image 1204 in FIG. 12(B) displays a treatment completion region 1205 specified on the basis of a result of step 903 performed for the first time. This is the same as the treatment prediction region 1203. The heat source arrangement optimization processing unit 106 analyzes a positional relationship among the treatment scheduled region 505, the treatment completion region 1205, and the blood vessels 503 in step 904 performed for the first time.

As displayed in the image 1204, in a case where there is a region which is included in the treatment scheduled region 505 but is not included in the treatment completion region 1205, it is determined that treatment is not completed in step 905 (step 905: No). In this case, the process returns to step 902, and a position of the next heat source is determined. An image 1206 in FIG. 12(C) displays, for example, a heat source 1207 in the second treatment determined in step 902 performed for the second time by the heat source arrangement optimization processing unit 106, and a treatment prediction region 1208 indicating a result predicted in step 903 performed for the second time.

The heat source arrangement optimization processing unit 106 in the third example determines a position of a heat source according to the same method as that for the first time in step 902 performed for the second and subsequent times. In the second heat transfer analysis, since a blood vessel included in the first treatment completion region 1205 is handled not to be present, the heat sink effect is reduced, and thus the second treatment prediction region 1208 generally tends to increase more than the first treatment completion region 1203.

The heat source arrangement optimization processing unit 106 sets the union between the treatment completion region 1205 indicating a result of prediction until the previous time and a treatment prediction region 1208 obtained through the present prediction, as the new treatment completion region 1205. The heat source arrangement optimization processing unit 106 analyzes a positional relationship among the new treatment completion region 1205, the treatment scheduled region 505, and the blood vessels 503 in step 904 performed for the second time.

According to the third example, a region in which the influence of the heat transfer effect such as the heat sink effect which is a factor to suppress a treatment effect is great is preferentially treated, and thus the influence of the heat transfer effect can be suppressed fast such that efficient treatment can be expected. Even if treatment is not enough, a region in which activity is high (for example, a region in which a blood vessel density is high) is treated in advance, and thus an effect to suppress recurrence risk and a recurrence rate can be expected.

The heat source arrangement optimization processing unit 106 may preferentially set a heat source at a position where the heat transfer effect is low in step 902. In this case, it can be expected that treatment in a wide range is completed in the first treatment.

In step 905 in the above-described example, the heat source arrangement optimization processing unit 106 determines that treatment is completed in a case where the entire treatment scheduled region set in step 901 is included in a treatment completion region, but may determine completion of treatment according to other conditions. For example, even if a part of a treatment scheduled region is not included in a treatment completion region yet, the heat source arrangement optimization processing unit 106 may determine that treatment is completed in a case where the number of times of repeatedly performing the steps 902 to 904 reaches a predetermined upper limit.

In a case where the above steps 902 to 904 are repeatedly performed, a heat source position determination method in step 902 may be changed. For example, a position of a heat source may be determined according to the method in the first example in step 902 performed for the first time, and a position of a heat source may be determined according to the method in the second example or the third example in step 902 performed for the second time. The same applies to other combinations.

As mentioned above, a description has been made of the processes performed by the treatment support apparatus 100 in order to support creation of a plan of treatment to be performed from now on before an operator starts treatment. The treatment support apparatus 100 may create a plurality of treatment plans while changing at least one of an initial condition and a computation method. Specifically, for example, the treatment support apparatus 100 may create a plurality of treatment plans in the first example or the second example while changing a position of a first heat source. Alternatively, a treatment plan in each of the first example to the third example may be created.

The treatment support apparatus 100 may output all of a plurality of created treatment plans, may output only treatment plans satisfying a predetermined condition, and may output only one treatment plan which is determined to be the best on the basis of a predetermined criterion. Specifically, for example, the treatment support apparatus 100 may evaluate each treatment plan on the basis of a predetermined criterion, so as to output all treatment plans, to output one or more treatment plans of which evaluation values are greater than a predetermined criterion value, and to output a treatment plan of which an evaluation value is the greatest.

In a case where a plurality of treatment plans are output, the treatment support apparatus 100 may also output information indicating a method of creating each treatment plan. The information indicating a creation method is, for example, information indicating that a position of a heat source enabling treatment to be performed in a wide range is preferentially determined (FIG. 10), information indicating that a position of a heat source is determined such that treatment is performed from an end of a treatment scheduled region (FIG. 11), and information indicating that a position of a heat source where the heat transfer effect is high is preferentially determined (FIG. 12). In a case where a plurality of treatment plans are output, the treatment support apparatus 100 may output the treatment plans in an order of greater evaluation values. Consequently, in a case where the plurality of treatment plans are displayed, determination bases used for an operator to select any treatment plan are provided, and thus a burden on the operator is reduced.

For example, an evaluation value may be set to become greater as the number of times of treatment (that is, the number of set heat sources) performed until the entire treatment scheduled region overlaps a predicted treatment completion region becomes smaller, and may be set to become greater as an overlapping portion between a treatment scheduled region and a predicted treatment completion region becomes larger in a case where an upper limit of the number of times of treatment is set. Consequently, it is possible to propose an appropriate treatment plan according to a condition of treatment.

The operator may refer to an output treatment plan, and may perform treatment without change by selecting a treatment plan in a case where a plurality of treatment plans are output, and may create a treatment plan by applying experience thereof to the output treatment plan.

The display unit 130 sequentially displays images as illustrated in FIGS. 5 to 8 and FIGS. 10 to 12 according to the progress of a process, and thus the operator can easily recognize a treatment plan, so that a burden on the operator is reduced.

Next, a description will be made of a process performed by the treatment support apparatus 100 after the operator starts treatment according to a treatment plan.

FIG. 13 is a flowchart illustrating an intraoperative process performed by the treatment support apparatus 100 according to the embodiment of the invention after the operator starts treatment.

First, the operator performs n-th treatment on an n-th heat source (step 1301). A heat source for the n-th treatment is referred to as an n-th heat source. An initial value of n is 1.

Next, the image generation processing unit 103 generates a blood vessel image (step 1302). This step corresponds to step 301 in FIG. 3.

Next, the heat source arrangement optimization processing unit 106 compares an actual treatment completion region specified from the blood vessel image generated in step 1302 with a treatment completion region at a time point where the n-th treatment is finished, predicted in the treatment plan (step 1303).

Next, the heat source arrangement optimization processing unit 106 determines whether or not treatment is completed on the basis of a result of the comparison in step 1303 (step 1304). For example, in a case where the entire treatment scheduled region is filled with the actual treatment completion region, the heat source arrangement optimization processing unit 106 may determine that treatment is completed. This determination may be performed by the operator on the basis of the blood vessel image generated in step 1302.

In a case where it is determined that treatment is not completed yet (step 1304: No), the heat source arrangement optimization processing unit 106 adjusts a position of an (n+1)-th heat source on the basis of the result of the comparison in step 1303, and displays a result thereof, and a final prediction result in the created treatment plan (step 1305).

The process returns to step 1301, and the operator performs n-th treatment on an n-th heat source with n+1 as new n.

In a case where it is determined that treatment is completed in step 1304 (step 1304: Yes), the intraoperative process is finished.

FIG. 14 is an explanatory diagram illustrating an intraoperative process performed by the treatment support apparatus 100 according to the embodiment of the invention.

An image 1401 indicates first treatment in a created treatment plan. Specifically, the image 1401 displays the treatment scheduled region 505, a first heat source 1402, and a treatment prediction region 1403 in the first treatment.

An image 1404 indicates a result of the first treatment performed according to the treatment plan. Specifically, the image 1404 displays an actual treatment completion region 1405 specified through blood vessel image generation (step 1302) after the first treatment is performed. As the accuracy of prediction becomes higher, a difference between the treatment prediction region 1403 and the actual treatment completion region 1405 is reduced. In the example illustrated in FIG. 14, a size of the actual treatment completion region 1405 is smaller than that of the treatment prediction region 1403.

The heat source arrangement optimization processing unit 106 compares the treatment prediction region 1403 with the actual treatment completion region 1405 (step 1303). In this example, since treatment of the entire treatment scheduled region 505 is not completed in the first treatment (step 1304: No), the heat source arrangement optimization processing unit 106 adjusts a position of a second heat source on the basis of a result of the comparison (steps 1305 and 1415).

An image 1410 displays a treatment completion region 1411. This is a treatment completion region predicted in a case where the second treatment and subsequent treatment are performed according to the initial treatment plan on the basis of the actual treatment completion region 1405 after the first treatment is performed. In the example illustrated in FIG. 14, as displayed in the image 1404, since the first actual treatment completion region 1405 is smaller than the first treatment prediction region 1403, the treatment completion region 1411 is smaller than the treatment scheduled region 505 so as to be included in the treatment scheduled region 505, and thus treatment deficiency 1412 not included in the treatment completion region 1411 occurs.

An image 1406 displays a heat source position 1407 before being corrected based on a result adjusted such that the treatment deficiency 1412 is removed, a heat source position 1408 after being corrected, and a treatment prediction region 1409 obtained through treatment on the heat source position 1408 after being corrected.

An image 1413 displays a treatment completion region 1414 predicted in a case where the second and subsequent treatment plans are corrected on the basis of the first actual treatment completion region 1405 as displayed in the image 1406. In this example, since the heat source position 1408 after being corrected is closer to the treatment deficiency 1412 than the heat source position 1407 before being corrected, the treatment deficiency 1412 is removed according thereto, and thus treatment of the entire treatment scheduled region 505 is predicted to be completed. Consequently, an error of prediction is removed, and thus reliable treatment is realized.

The above-described adjustment (correction) of a treatment plan based on an actual treatment result may be realized according to various methods, and some of the methods will now be described.

FIG. 15 is an explanatory diagram illustrating a first example of the intraoperative process performed by the treatment support apparatus 100 according to the embodiment of the invention.

In a case where a plurality of times of treatment are performed according to a created treatment plan, an error between a treatment prediction region in each piece of treatment at the time of creation of the treatment plan and a treatment completion region after each piece of actual treatment is performed is accumulated whenever the treatment is repeatedly performed. Thus, there is a probability that a residual region (that is, a region not included in an actual treatment completion region in a treatment scheduled region) which is not expected may be present at the time at which all pieces of the planned treatment are finished. Also in the middle of treatment, there is a probability that deficiency and excess of treatment may occur for the reason why, for example, a blood vessel which is to disappear through treatment hitherto remains (or conversely, a blood vessel which is to remain disappears through treatment hitherto). In the example illustrated in FIG. 15, all pieces of treatment are performed according to a treatment plan created initially (that is, before first treatment is started) regardless of a result of each piece of treatment actually performed (step 1505), and, then, in a case where there is a residual region of which treatment is not finished, a treatment plan for treating the region is added.

The images 1401 and 1404 illustrated in FIG. 15 are respectively the same as those illustrated in FIG. 14. An image 1501 displays a residual region 1502 at the time at which the first treatment is finished. The residual region 1502 is a difference obtained by subtracting the actual treatment completion region 1405 at the time at which the first treatment is finished from the treatment scheduled region 505, and is displayed by half-tone dot meshing in the image 1501.

In the example illustrated in FIG. 15, even if the treatment completion region 1405 does not match the treatment prediction region 1403, all pieces of planned treatment are performed without changing subsequent treatment plans. An image 1503 displays a residual region 1504 at the time at which all pieces of the planned treatment are finished, with half-tone dot meshing. The treatment support apparatus 100 creates an additional treatment plan for treating the residual region 1504. Specifically, the treatment support apparatus 100 sets the residual region 1504 as a new treatment scheduled region, and creates an additional treatment plan by performing the processes in steps 301 to 307 in FIG. 3.

Thereafter, the treatment support apparatus 100 and the operator perform the same processes as described above according to the additional treatment plan. The above-described creation of a treatment plan by the treatment support apparatus 100 and treatment performed by the operator on the basis of the treatment plan may be repeatedly performed until the residual region disappears.

According to the example illustrated in FIG. 15, an additional treatment plan is not created until all pieces of planned treatment are finished. If the accuracy of predicting a treatment completion region is sufficiently high, there is a case where an additional treatment plan is not required to be created. Thus, an increase in computation cost is suppressed. However, in a case where the accuracy of predicting a treatment completion region is low, there is a tendency that the number of heat sources to be disposed increases due to an additional treatment plan.

FIG. 16 is an explanatory diagram illustrating a second example of the intraoperative process performed by the treatment support apparatus 100 according to the embodiment of the invention.

In the example illustrated in FIG. 16, whenever one time of treatment is performed, the next and subsequent treatment plans are recreated on the basis of actual results.

The images 1401, 1404 and 1501 illustrated in FIG. 16 are respectively the same as those illustrated in FIG. 15. The treatment support apparatus 100 recreates the second and subsequent treatment plans on the basis of the residual region 1502 at the time at which the first treatment is finished. Specifically, the treatment support apparatus 100 sets the residual region 1502 as a new treatment scheduled region, and recreates the second and subsequent treatment plans by performing the processes in steps 301 to 307 in FIG. 3 (step 1601). Alternatively, the operator may manually determine a treatment plan by referring to the treatment plan image displayed in step 307. The operator performs the second treatment according to the treatment plan (step 1602). For example, the heat source position 1408 after being corrected in the example illustrated in FIG. 14 may be created in the above-described way.

Next, the treatment support apparatus 100 checks an effect of the second treatment (step 1603). This process may be performed in the same manner as, for example, in steps 1302 to 1304 in FIG. 13. Thereafter, the above-described creation of a treatment plan in the treatment support apparatus 100 and treatment performed by the operator on the basis of the treatment plan may be repeatedly performed until the residual region disappears.

According to the example illustrated in FIG. 16, since the next and subsequent treatment plans are reexamined whenever treatment is performed, and thus an error is minimized, accuracy is the highest, and the number of disposed heat sources can be minimized. On the other hand, computation cost increases, but this is considered to be supplemented with the normal computer capability. In a case where the operator creates a treatment plan, time and effort to create the treatment plan increase, but, for example, the operator may select a preoperative optimization method, and creation of a treatment plan may be automated by optimizing a treatment plan by using the method. A method selected here may be one of, for example, the methods described with reference to FIGS. 10 to 12.

As described above, the treatment support apparatus 100 of the present embodiment may be realized by using an MM apparatus or an X-ray CT apparatus in addition to an ultrasonic diagnosis apparatus. However, if the ultrasonic diagnosis apparatus is used, since an image of a treatment scheduled region is observed in real time, in a case where a plurality of times of treatment are planned as described above, it is possible to easily perform an intraoperative process in which an image of a result of each time of treatment is observed right after the treatment, and is reflected in the next treatment. Since the apparatus is small-sized, and has no invasive property such as radiation exposure, treatment work efficiency is improved, and physical burdens on an operator and a patient can be reduced.

The invention is not limited to the above Examples, and includes a plurality of modification examples. The above Examples have been described in detail for better understanding of the invention, and thus are not necessarily limited to including all of the above-described configurations.

Some or all of the above-described respective configurations, functions, processing units, processing means, and the like may be designed as, for example, integrated circuits so as to be realized in hardware. The above-described respective configurations and functions may be realized in software by a processor interpreting and executing a program for realizing each function. Information regarding a program, a table, a file, and the like for realizing each function may be stored in a storage device such as a nonvolatile semiconductor memory, a hard disk drive, or a solid state drive (SSD), or a non-transitory computer readable data storage medium such as an IC card, an SD card, and a DVD.

A control line or an information line which is necessary for description is illustrated, and all control lines or information lines on a product may not necessarily be illustrated. It may be considered that almost all of the configurations are actually connected to each other.

The invention claimed is:

1. A treatment support apparatus comprising:
   a processor; and
   a storage device connected to the processor,
   wherein the storage device holds image information of tissue in a living body of a treatment target, and
   wherein the processor
      extracts a blood vessel structure of the inside of the living body from the image information,
      specifies a region in which a predicted temperature is included in a predetermined range as a treatment prediction region in which thermal treatment is predicted to be completed on a treatment scheduled region,
      calculates positions of one or more heat sources for the thermal treatment and an order of preforming the thermal treatment such that a size of an overlapping portion between the treatment prediction region and the treatment scheduled region is increased, the thermal treatment scheduled region including at least a part of the extracted blood vessel structure on the basis of the extracted blood vessel structure, and
      outputs data for displaying an image including the calculated positions of the one or more heat sources.

2. The treatment support apparatus according to claim 1, wherein the processor
   computes thermal conduction in the living body, and heat convection due to a blood flow based on the extracted blood vessel structure, so as to predict a temperature distribution in the living body in a case where thermal treatment is performed on the positions of the one or more heat sources, and outputs data for displaying an image including the calculated order.

3. The treatment support apparatus according to claim 2, wherein the processor calculates the positions of the one or more heat sources such that the entire treatment scheduled region is included in the treatment prediction region, and the number of heat sources is minimized.

4. The treatment support apparatus according to claim 2, wherein the processor calculates the positions of the one or more heat sources such that the number of heat sources is equal to or smaller than a predetermined upper limit, and the size of the overlapping portion between the treatment prediction region and the treatment scheduled region is maximized.

5. The treatment support apparatus according to claim 2, wherein the processor specifies the treatment prediction region in a case where thermal treatment is performed on a position of an initial heat source, predicts a blood vessel structure which changes due to the thermal treatment on the position of the initial heat source in a case where the treatment scheduled region includes a residual region not overlapping the specified treatment prediction region, and specifies the treatment prediction region in a case where thermal treatment is performed on a position of the next heat source on the basis of the predicted blood vessel structure.

6. The treatment support apparatus according to claim 5, wherein the processor preferentially calculates a position where a treatment prediction region is increased in a case where thermal treatment is performed, as the position of the heat source.

7. The treatment support apparatus according to claim 5, wherein the processor preferentially calculates a position where a boundary of a treatment prediction region comes close to a boundary of the residual region in a case where thermal treatment is performed, as the position of the heat source.

8. The treatment support apparatus according to claim 5, wherein the processor preferentially calculates a position where an effect of the heat convection due to a blood flow is considerable, as the position of the heat source.

9. The treatment support apparatus according to claim 2, wherein the processor determines whether or not there is a residual region of which the thermal treatment is not completed in the treatment scheduled region on the basis of image information of tissue in the living body after actual thermal treatment is performed on at least one of the one or more heat sources, and sets the residual region as a new treatment scheduled region in a case where there is the residual region, and calculates positions of one or more heat sources for thermal treatment on the new treatment scheduled region on the basis of image information of tissue in the living body after actual thermal treatment is performed on at least one of the one or more heat sources.

10. The treatment support apparatus according to claim 9, wherein the processor determines whether or not there is a residual region of which the thermal treatment is not completed in the treatment scheduled region on the basis of image information of tissue in the living body after actual thermal treatment is performed on all of the one or more heat sources.

11. The treatment support apparatus according to claim 9, wherein the processor determines whether or not there is a residual region of which the thermal treatment is not completed in the treatment scheduled region on the basis of image information of tissue in the living body after actual thermal treatment is performed on one of the heat sources according to the calculated order.

12. The treatment support apparatus according to claim 1, wherein the thermal treatment is performed by heating or cooling the one or more heat sources.

13. A treatment support apparatus comprising:

a processor;

a storage device connected to the processor; and a display unit connected to the processor, wherein the storage device holds image information of tissue in a living body of a treatment target, and wherein the processor extracts a blood vessel structure of the inside of the living body from the image information, and a treatment scheduled region including at least a part of the extracted blood vessel structure is set, computes thermal conduction in the living body, and heat convection due to a blood flow based on the extracted blood vessel structure, so as to predict a temperature distribution in the living body in a case where thermal treatment is performed on positions of one or more heat sources, specifies a region in which a predicted temperature is included in a predetermined range as a treatment prediction region in which thermal treatment is predicted to be completed, and calculates the positions of the one or more heat sources and an order of performing the thermal treatment such that a size of an overlapping portion between the treatment prediction region and the treatment scheduled region is increased, and wherein the display unit sequentially displays an image of the extracted blood vessel structure, an image of the treatment scheduled region, an image indicating a temperature distribution in the living body predicted in each piece of thermal treatment in a case where thermal treatment is performed on the calculated positions of the heat sources according to the calculated order, and an image of a treatment prediction region specified on the basis of the temperature distribution.

14. A treatment support method executed by a computer including a processor, and a storage device connected to the processor, the storage device holding image information of tissue in a living body of a treatment target, the method comprising:

a step of causing the processor to extract a blood vessel structure of the inside of the living body from the image information;

a step of causing the processor to specify a region in which a predicted temperature is included in a predetermined range as a treatment prediction region in which thermal treatment is predicted to be completed on a treatment scheduled region, a step of causing the processor to calculate positions of one or more heat sources for the thermal treatment and an order of preforming the thermal treatment such that a size of an overlapping portion between the treatment prediction region and the treatment scheduled region is increased, the thermal treatment scheduled region including at least a part of the extracted blood vessel structure on the basis of the extracted blood vessel structure; and a step of causing the processor to output data for displaying an image including the calculated positions of the one or more heat sources.

* * * * *